United States Patent
Zhu et al.

(10) Patent No.: US 11,058,476 B2
(45) Date of Patent: Jul. 13, 2021

(54) SYSTEMS AND METHODS FOR X-RAY IMAGING

(71) Applicant: SHANGHAI UNITED IMAGING HEALTHCARE CO., LTD., Shanghai (CN)

(72) Inventors: Guoping Zhu, Shanghai (CN); Tieshan Zhang, Shanghai (CN); Xu Chu, Shanghai (CN); Fan Zhao, Shanghai (CN); Zhihui Shu, Shanghai (CN); Jinglin Wu, Shanghai (CN); Bin Cao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 23 days.

(21) Appl. No.: 16/666,435

(22) Filed: Oct. 29, 2019

(65) Prior Publication Data

US 2020/0337759 A1 Oct. 29, 2020

(30) Foreign Application Priority Data

Apr. 24, 2019 (CN) .......................... 201910335863.7

(51) Int. Cl.
| | |
|---|---|
| *A61B 6/00* | (2006.01) |
| *A61B 6/03* | (2006.01) |
| *A61B 18/12* | (2006.01) |
| *A61B 6/02* | (2006.01) |

(52) U.S. Cl.
CPC .......... *A61B 18/1206* (2013.01); *A61B 6/027* (2013.01); *A61B 6/03* (2013.01); *A61B 6/40* (2013.01); *A61B 6/54* (2013.01)

(58) Field of Classification Search
CPC ....... A61B 18/1206; A61B 6/027; A61B 6/03; A61B 6/40; A61B 6/54; A61B 6/482; A61B 6/48
See application file for complete search history.

(56) References Cited

U.S. PATENT DOCUMENTS

| | | | |
|---|---|---|---|
| 4,216,382 A | 8/1980 | Franke | |
| 5,602,897 A | 2/1997 | Kociecki et al. | |
| 2007/0274457 A1 | 11/2007 | Dunham et al. | |
| 2008/0130323 A1 | 6/2008 | Wagner et al. | |
| 2016/0192466 A1* | 6/2016 | Larroux | H05G 1/32 378/112 |
| 2017/0086775 A1 | 3/2017 | Madhav et al. | |
| 2021/0007210 A1 | 1/2021 | Steadman Booker et al. | |

* cited by examiner

*Primary Examiner* — Courtney D Thomas
(74) *Attorney, Agent, or Firm* — Metis IP LLC

(57) ABSTRACT

The present disclosure relates to systems and methods for energy imaging. The method may include obtaining a reference waveform of a tube voltage of a radiation source of a scanner. The reference waveform may be formed based on a superposition of a sine wave and one or more harmonics corresponding to the sine wave. The method may include causing a high voltage generator to generate the tube voltage changing between a first voltage and a second voltage lower than the first voltage according to the reference waveform. The tube voltage may be provided to the radiation source for generating radiation rays. The method may further include causing the scanner to perform energy imaging.

20 Claims, 13 Drawing Sheets

SYSTEMS AND METHODS FOR X-RAY IMAGING

CROSS-REFERENCE TO RELATED APPLICATIONS

This application claims priority to Chinese Patent Application No. 201910335863.7, filed on Apr. 24, 2019, the contents of which are hereby incorporated by reference.

TECHNICAL FIELD

The present disclosure generally relates to X-ray imaging fields, and in particular, to systems and methods for energy imaging.

BACKGROUND

X-ray imaging has been widely used in medical diagnosis, radiotherapy planning, surgery planning, and other medical procedures. For example, energy imaging techniques for X-ray imaging are used to distinguish different substances of a subject based on the energy dependence of attenuation coefficients of different substances. Using an energy imaging technique (e.g., a dual-energy imaging technique), a high voltage generator may be used to provide a tube voltage changing between a low voltage to a high voltage to a radiation source for generating radiation rays. However, the changing of the tube voltage between the low voltage to the high voltage includes a rising transition time and a falling transition time which may reduce a degree of difference of energy spectrums of the radiation rays, thereby influencing the quality of one or more images generated using the energy imaging technique. Therefore, it is desirable to provide a reference waveform of a tube voltage to guide the voltage transition that can improve a degree of difference of energy spectrums and be easily realized.

SUMMARY

According to an aspect of the present disclosure, a system for energy imaging is provided. The system may include at least one storage device storing executable instructions and at least one processor in communication with the at least one storage device. When executing the executable instructions, the at least one processor may cause the system to perform the following operations. The system may obtain a reference waveform of a tube voltage of a radiation source of a scanner. The reference waveform may be formed based on a superposition of a sine wave and one or more harmonics corresponding to the sine wave. A frequency of at least one of the one or more harmonics may be an integer multiple of a frequency of the sine wave. The system may cause a high voltage generator to generate the tube voltage changing according to the reference waveform. For example, the tube voltage may change between a first voltage and a second voltage lower than the first voltage. The tube voltage may be provided to the radiation source for generating radiation rays. The system may further cause the scanner to perform energy imaging. For example, the system may obtain projection data generated by detecting at least a portion of the radiation rays by a detector of the scanner.

In some embodiments, to obtain a reference waveform of a tube voltage of a radiation source of a scanner, the system may determine the frequency of the sine wave and a frequency of each of the one or more harmonics. The system may determine an amplitude of the sine wave and an amplitude of each of the one or more harmonics. The system may determine the reference waveform of the tube voltage based on the frequency and the amplitude of each of the one or more harmonics and the frequency and the amplitude of the sine wave.

In some embodiments, to determine the frequency of the sine wave and a frequency of each of the one or more harmonics, the system may determine the frequency of the sine wave based on a rotation speed of a gantry of the scanner where the radiation source is installed. The system may determine a maximum frequency of the one or more harmonics based on the frequency of the sine wave. The system may determine the frequency of each of the one or more harmonics at least based on in part the maximum frequency of the one or more harmonics. The maximum frequency of the one or more harmonics may be lower than a frequency threshold.

In some embodiments, the frequency threshold may be defined by a tracking ability of a controller of the high voltage generator for tracking the tube voltage.

In some embodiments, to determine an amplitude of the sine wave and an amplitude of each of the one or more harmonics, the system may determine the amplitude of the sine wave and the amplitude of each of the one or more harmonics based on the frequency of each of the one or more harmonics. The amplitude of each of the one or more harmonics and the amplitude of the sine wave may be such that one or more maximum values of the reference waveform are equal to the first voltage or one or more minimum values of the reference waveform are equal to the second voltage.

In some embodiments, a declining speed of the tube voltage when the tube voltage changes from the first voltage to the second voltage according to the reference waveform may be lower than a speed threshold.

In some embodiments, the speed threshold may be determined based on an output capacitance of the high voltage generator and a tube current of the radiation source.

In some embodiments, a degree of difference between energy spectrums of radiation rays generated based on the tube voltage changing between the first voltage and the second voltage according to the reference waveform may exceed a threshold.

In some embodiments, the threshold may be determined based on a degree of difference between energy spectrums of radiation rays generated based on the tube voltage changing between the first voltage and the second voltage according to a sinusoidal waveform.

In some embodiments, the system may obtain a first portion of the projection data corresponding to the first voltage (i.e., a maximum value of the tube voltage). The system may obtain a second portion of the projection data corresponding to the second voltage (i.e., a minimum value of the tube voltage). The system may generate one or more images based on the first portion of the projection data and the second portion of the projection data.

In some embodiments, the system may further generate one or more images based on the projection data using an energy imaging technique.

According to another aspect of the present disclosure, an imaging device may be provided. The imaging device may include a high voltage generator configured to generate a tube voltage changing between a first voltage and a second voltage according to a reference waveform. The imaging device may include a radiation source configured to generate radiation rays when the tube voltage is provided to the radiation source. The reference waveform may be formed based on a superposition of a sine wave and one or more harmonics corresponding to the sine wave. A frequency of one of the one or more harmonics may be an integer multiple of a frequency of the sine wave. The imaging device may include a detector configured to detect at least a portion of the radiation rays to generate projection data.

According to another aspect of the present disclosure, a method for energy imaging may be provided. The method may be implemented on a computing device having at least one processor and at least one storage device. The method may include obtaining a reference waveform of a tube voltage of a radiation source of a scanner. The reference waveform may be formed based on a superposition of a sine wave and one or more harmonics corresponding to the sine wave. A frequency of at least one of the one or more harmonics may be an integer multiple of a frequency of the sine wave. The method may also include causing a high voltage generator to generate the tube voltage changing according to the reference waveform. The tube voltage may be provided to the radiation source for generating radiation rays. The method may further include causing the scanner to perform energy imaging.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
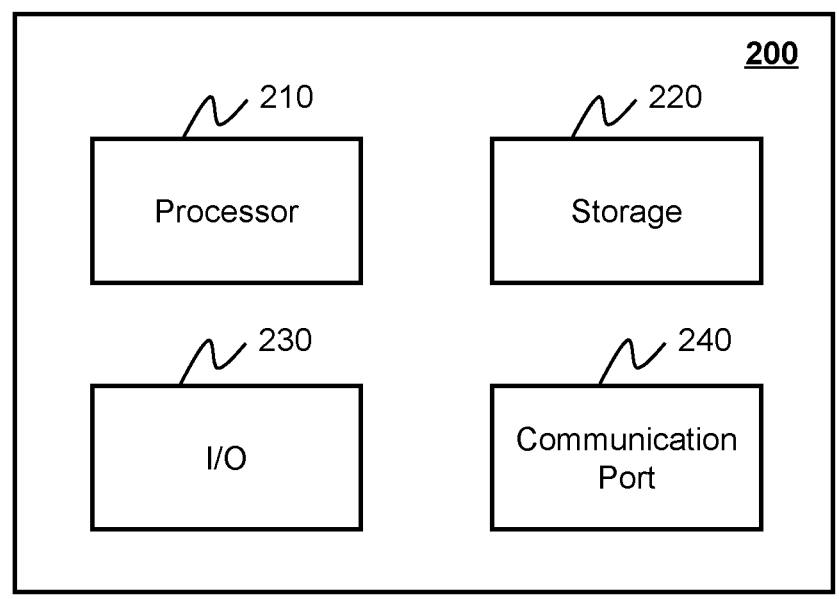
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

Provided herein are systems and methods for energy imaging. A system may include at least one storage device storing executable instructions, and at least one processor in communication with the at least one storage device. When executing the executable instructions, the at least one processor may cause the system to obtain a reference waveform of a tube voltage of a radiation source of a scanner. The at least one processor may cause a high voltage generator to provide the tube voltage changing between a first voltage and a second voltage lower than the first voltage according to the reference waveform. The tube voltage may be provided to the radiation source for generating radiation rays. The at least one processor may cause the system to obtain projection data generated by detecting at least a portion of the radiation rays by a detector of the scanner. The reference waveform may be formed based on a superposition of a sine wave and one or more harmonics corresponding to the sine wave. A frequency of at least one of the one or more harmonics may be an integer multiple of a frequency of the sine wave. A reference waveform including a superposition of the sine wave and one or more harmonics may improve a degree of difference of different X-ray energy spectrums corresponding to the reference waveform with respect to other waveforms, such as a sine waveform, a triangular wave, etc. thereby improving quality of images generated based on the radiation rays different X-ray energy spectrums. The system may determine a frequency and/or amplitude of the sine wave and a frequency and/or amplitude of each of the one or more harmonics at least in part based on a tracking ability of a controller of the high voltage generator for tracking the tube voltage, which may cause the reference waveform to be implemented by the high voltage generator easily for providing the tube voltage changing between a high voltage and a low voltage with respect to a rectangular waveform, a trapezoidal wave, etc.

Figure 1:
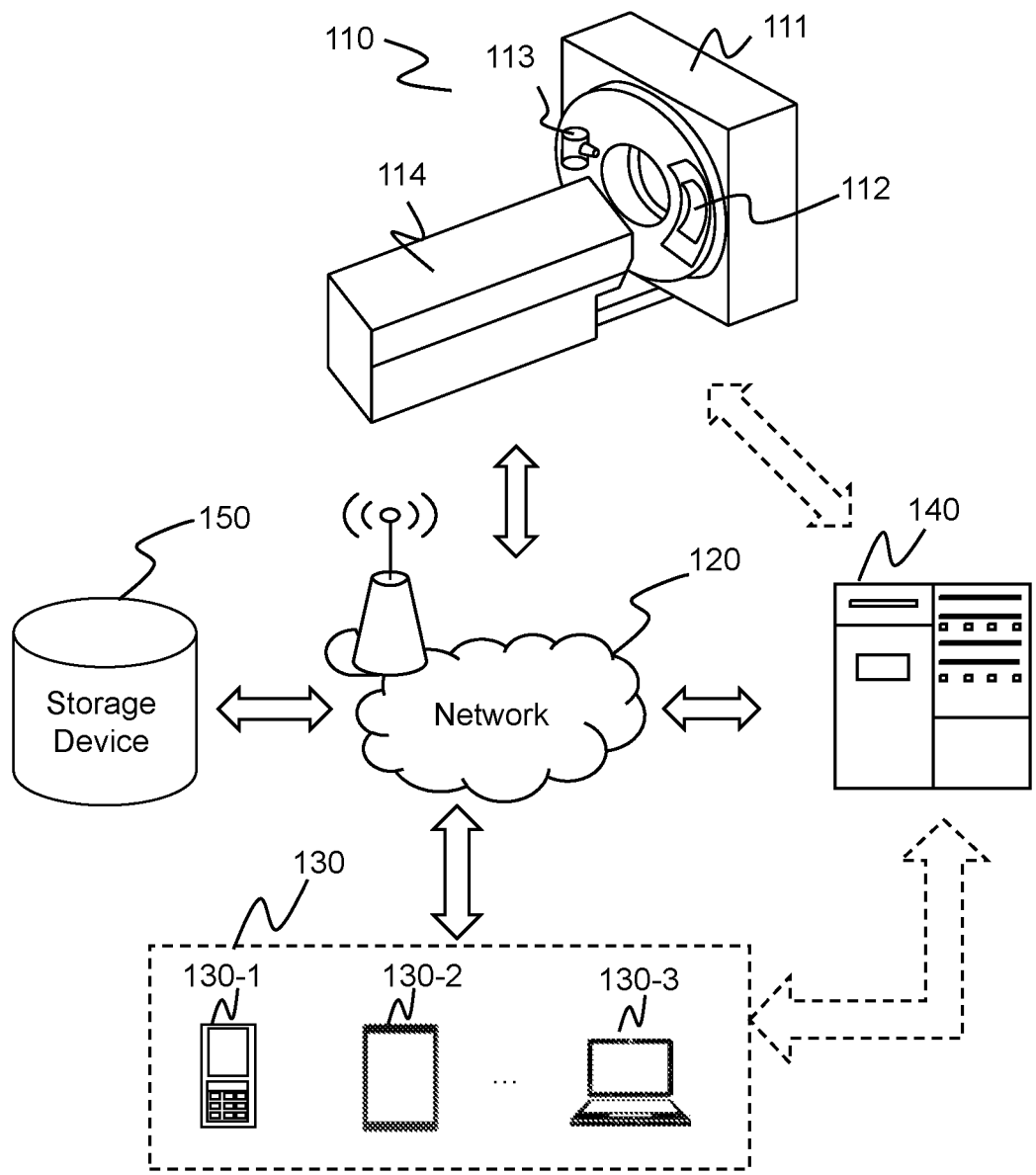
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. In some embodiments, the imaging system 100 may be applied to any application scenario in which radiation rays (e.g., X-rays) are used for generating images and/or providing treatment, such as a computed tomography (CT) system, a digital radiography (DR) system, a C-arm X-ray system, a computed tomography-positron emission tomography (CT-PET) system, or the like, or a combination thereof.

As illustrated in FIG. 1, the imaging system 100 may include an imaging device 110, a network 120, one or more terminals 130, a processing device 140, and a storage device 150. The components in the imaging system 100 may be connected in one or more of various ways. Merely by way of example, the imaging device 110 may be connected to the processing device 140 through the network 120. As another example, the imaging device 110 may be connected to the processing device 140 directly as indicated by the bi-directional arrow in dotted lines linking the imaging device 110 and the processing device 140. As a further example, the storage device 150 may be connected to the processing device 140 directly or through the network 120. As still a further example, the terminal(s) 130 may be connected to the processing device 140 directly (as indicated by the bi-directional arrow in dotted lines linking the terminal(s) 130 and the processing device 140) or through the network 120.

The imaging device 110 may be configured to scan a subject using radiation rays and generate imaging data used to generate one or more images relating to the subject. In some embodiments, the imaging device 110 may transmit the imaging data to the processing device 140 for further processing (e.g., generating one or more images). In some embodiments, the imaging data and/or the one or more images associated with the subject may be stored in the storage device 150 and/or the processing device 140. In some embodiments, the imaging device 110 may include a computed tomography (CT) scanner, a digital radiography (DR) scanner, a C-arm X-ray scanner, a digital subtraction angiography (DSA) scanner, a dynamic spatial reconstructor (DSR) scanner, an X-ray microscopy scanner, a multi-modality scanner, or the like, or a combination thereof. Exemplary multi-modality scanners may include a computed tomography-positron emission tomography (CT-PET) scanner, a computed tomography-magnetic resonance imaging (CT-MRI) scanner, etc.

The imaging device 110 may include a gantry 111, one or more detectors 112, a radiation source 113, and a table 114.

The gantry 111 may be configured to provide support for other components (e.g., the radiation source 113, the detector(s) 112, etc.) of the imaging device 110. In some embodiments, the detector(s) 112 and the radiation source 113 may be oppositely mounted on the gantry 111. In some embodiments, the gantry 111 may rotate and/or move. The detector(s) 112 and the radiation source 113 may rotate along with the rotation of the gantry 111. The table 114 may be configured to locate and/or support an object. The object may be placed on the table 114 and moved into a detection tunnel (e.g., a space between the detectors 112 and the radiation source 113) of the imaging device 110. The object may be biological or non-biological. Merely by way of example, the object may include a patient, a man-made object, etc. As another example, the object may include a specific portion, organ, and/or tissue of the patient. For example, the object may include head, brain, neck, body, shoulder, arm, thorax, cardiac, stomach, blood vessel, soft tissue, knee, feet, or the like, or any combination thereof. In the present disclosure, "subject", "object" or "scanned object" are used interchangeably.

The radiation source 113 may be configured to generate and/or emit radiation rays to scan an object that is placed on the table 114. In some embodiments, the radiation source 113 may include one or more tubes, a high voltage generator, or any other component (e.g., a collimator). The high voltage generator may be configured to provide a tube voltage and/or a tube current for the tube, and/or provide power for other components of the radiation source 113. The high voltage generator may include a controller, an inverter circuit, a high voltage generating circuit, a rectifier, or any other modules (e.g., a driving circuit). The controller may be configured to control and/or monitor one or more components (e.g., the inverter circuit) of the high voltage generator. For example, the controller may control the inverter circuit to provide the tube voltage changing between a first voltage and a second voltage lower than the first voltage according to a reference waveform to the radiation source 113 for generating radiation rays. The reference waveform may be determined by the processing device 140. As another example, the controller may be configured to track and detect actual values (i.e., feedback values) of the tube voltage and transmit the feedback values of the tube voltage to the processing device 140 or any other components of the imaging system 100. The inverter circuit may be configured to convert a direction voltage provided by a direct power into an alternating voltage. The high voltage generating circuit may be configured to increase the alternating voltage to obtain an increased alternating voltage. The rectifier may be configured to convert the increased alternating voltage into a high direct voltage (i.e., the tube voltage).

The tube may be configured to generate radiation rays when the high voltage generator applies the tube voltage to the tube. In some embodiments, the tube may include an anode target and a cathode filament. The cathode filament may be configured to generate electrons. The anode target may be configured to generate the radiation rays (e.g., X-rays) when the electrons impinge on the anode target. When the tube voltage is applied by the high voltage generator between an anode and a cathode of the tube. An electric field may be generated between the anode and the cathode of the tube. In some embodiments, the high voltage generator may also supply a current to the cathode filament of the tube for heating the cathode filament to generate hot electrons. The hot electrons may impinge the anode target under the electric field between the anode and the cathode. Then radiation rays may be generated by the anode target in response to receipt of the electron beam. The anode target may be driven to rotate for dissipating and/or reducing heat generated by the electron beam impinging the anode target.

The detector 112 may receive at least a portion of the radiation rays generated by the radiation source 113. In some embodiments, the imaging device 110 may include one single detector which may be configured to detect the at least a portion of the radiation rays emitted by the radiation source 113 when the tube voltage of the tube changes between a first voltage and a second voltage lower than the first voltage. In some embodiments, the imaging device 110 may include two detectors. One detector may be configured to detect a first portion of the radiation rays emitted by the radiation source 113 responding to the first voltage, and another detector may be configured to detect a second portion of the radiation rays emitted by the radiation source 113 responding to the second voltage lower than the first voltage. In some embodiments, the detector(s) 112 may include a plurality of detector units, which may be arranged in any suitable manner, for example, a channel direction and a row direction. The detector 112 may include a scintillation detector (e.g., a cesium iodide detector), a gas detector, etc.

The network 120 may facilitate the exchange of information and/or data. In some embodiments, one or more components of the imaging system 100 (e.g., the imaging device 110, the terminal 130, the processing device 140, or the storage device 150) may send information and/or data to another component(s) in the imaging system 100 via the network 120. For example, the processing device 140 may obtain a reference waveform of the tube voltage of the tube, via the network 120 from the storage device 150. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, changes, server computers, and/or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone changed network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the imaging system 100 may be connected to the network 120 to exchange data and/or information.

The terminal(s) 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal(s) 130 may remotely operate the imaging device 110. In some embodiments, the terminal 130 may operate the imaging device 110 via a wireless connection. In some embodiments, the terminal(s) 130 may receive information and/or instructions inputted by a user, and send the received information and/or instructions to the imaging device 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the imaging device 110, the terminal 130, or the storage device 150. For example, the processing device 140 may obtain a reference waveform of a tube voltage of a radiation source of a scanner (e.g., the imaging device 110). The reference waveform may be formed based on a superposition of a sine wave and one or more harmonics corresponding to the sine wave. A frequency of at least one of the one or more harmonics may be an integer multiple of a frequency of the sine wave. The processing device 140 may cause a high voltage generator of an imaging device (e.g., the imaging device 110) to provide the tube voltage by changing between a first voltage and a second voltage lower than the first voltage according to the reference waveform to the radiation source for generating radiation rays. The processing device 140 may obtain projection data generated by detecting at least a portion of the radiation rays by a detector of the scanner (e.g., the imaging device 110). The processing device 140 may be a central processing unit (CPU), a digital signal processor (DSP), a system on a chip (SoC), a microcontroller unit (MCU), or the like, or any combination thereof.

In some embodiments, the processing device 140 may be a single server or a server group. The server group may be centralized or distributed. In some embodiments, the processing device 140 may be local or remote. For example, the processing device 140 may access information and/or data stored in the imaging device 110, the terminal 130, and/or the storage device 150 via the network 120. As another example, the processing device 140 may be directly connected to the imaging device 110, the terminal 130, and/or the storage device 150, to access the stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal(s) 130 and/or the processing device 140. For example, the storage device 150 may store one or more images obtained from the processing device 140. In some embodiments, the storage device 150 may store data and/or instructions that the processing device 140 may execute or use to perform exemplary methods described in the present disclosure. For example, the storage device 150 may store data and/or instructions that the processing device 140 may execute or use to generate one or more images based on image data generated by the imaging device 110. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the imaging system 100 (e.g., the terminal(s) 130, the processing device 140). One or more components of the imaging system 100 may access the data or instructions stored in the storage device 150 via the network 120. In some embodiments, the storage device 150 may be directly connected to or communicate with one or more components of the imaging system 100 (e.g., the terminal 130, the processing device 140). In some embodiments, the storage device 150 may be part of the processing device 140.

FIG. 2 is a schematic diagram illustrating hardware and/or software components of an exemplary computing device according to some embodiments of the present disclosure. As illustrated in FIG. 2, the computing device 200 may include a processor 210, a storage 220, an input/output (I/O) 230, and a communication port 240. In some embodiments, the processing device 140 and/or the terminal 130 may be implemented on the computing device 200.

The processor 210 may execute computer instructions (program code), and when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the imaging device 110, the terminal 130, the storage device 150, and/or any other component of the imaging system 100. For example, the processor 210 may process one or more voltage waves from the storage imaging device 110 to generate a superposed waveform. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operations A and B, it should be understood that operations A and B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the terminal 130, the storage device 150, or any other component of the imaging system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program (e.g., in the form of computer-executable instructions) for the processing device 140 for obtaining projection data for scanning a subject. As another example, the storage 220 may store a program (e.g., in the form of computer-executable instructions) for the processing device 140 for determining a reference waveform relating to one or more voltages.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the imaging device 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
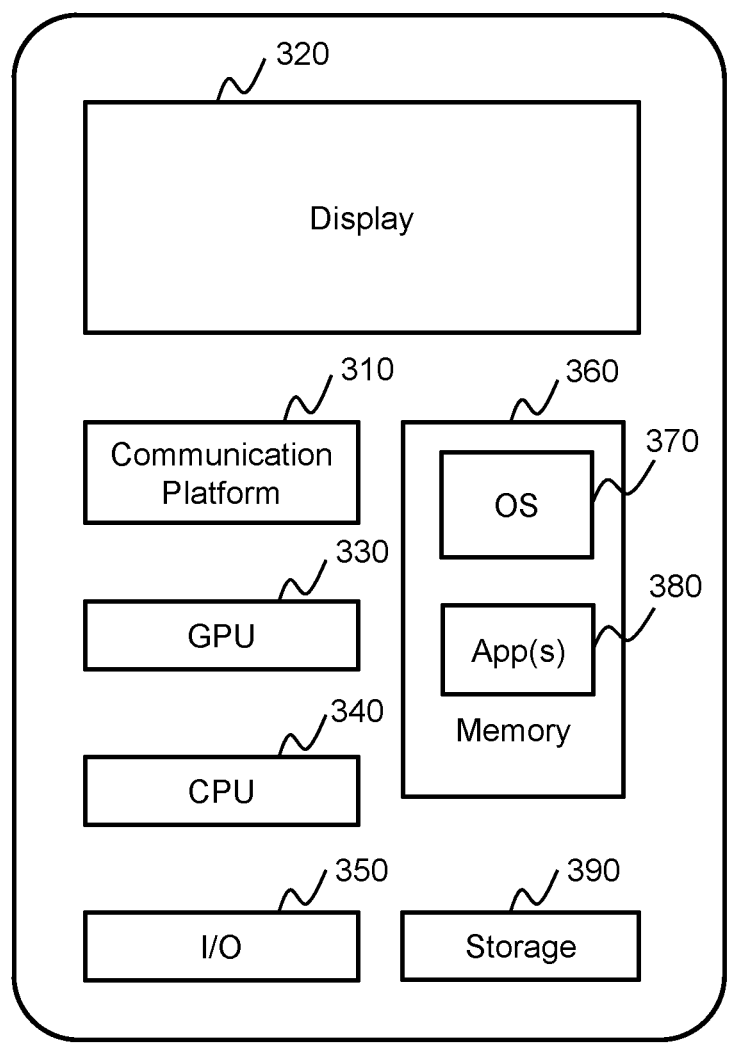
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device according to some embodiments of the present disclosure. In some embodiments, the processing device 140 and/or the terminal(s) 130 may be implemented on the mobile device 300. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image of an object as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
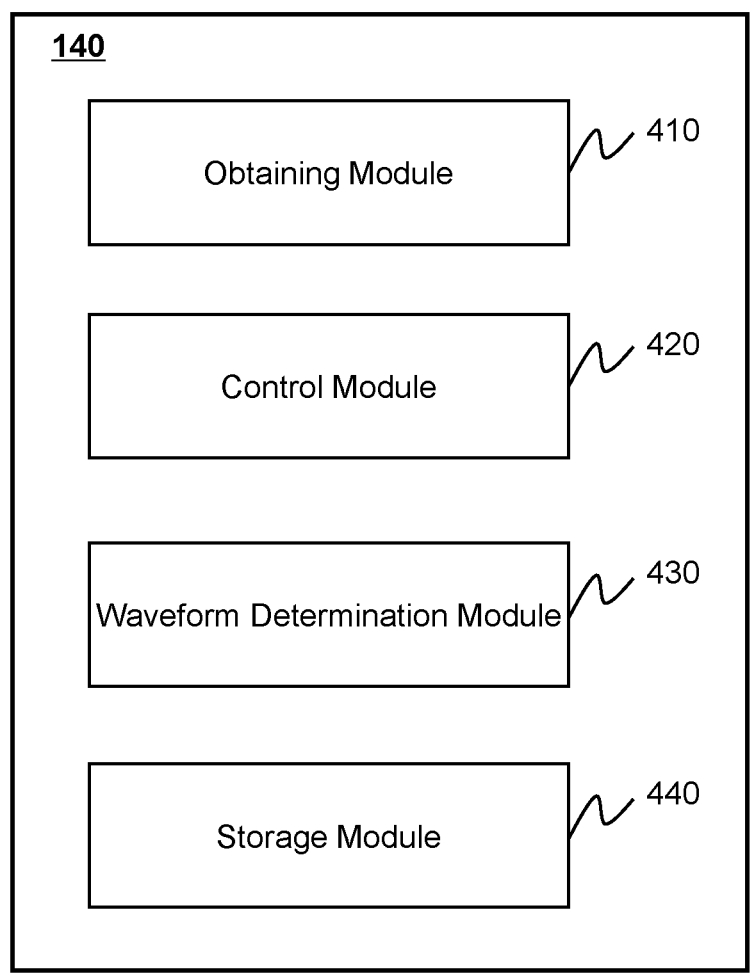
FIG. 4 is a block diagram illustrating an exemplary processing device according to some embodiments of the present disclosure.

FIG. 4 is a block diagram illustrating an exemplary processing device 140 according to some embodiments of the present disclosure. The processing device 140 may include an obtaining module 410, a control module 420, a reference waveform determination module 430, and a storage module 440.

The obtaining module 410 may be configured to obtain data or information regarding energy imaging. For example, the obtaining module 140 may obtain a reference waveform of a tube voltage of a radiation source of a scanner. The reference waveform may be used to describe a change of the tube voltage with time. The reference waveform may be formed by superposing a sine wave and one or more harmonics. The tube voltage may be provided to the radiation source for generating radiation rays. In some embodiments, the obtaining module 410 may obtain projection data from the scanner generated by detecting at least a portion of the radiation rays using one or more detectors of the scanner. The projection data may indicate attenuation of at least portion of the radiation rays passing through the subject.

The control module 420 may be configured to control one or more components of the imaging system 100. For example, the control module 420 may cause a high voltage generator to generate the tube voltage changing between a high voltage and a low voltage according to the reference waveform to the radiation source for generating the radiation rays. As another example, the control module 420 may control the obtaining module 410 to obtain the reference waveform from the storage module 440.

The waveform determination module 430 may be configured to determine the reference waveform. For example, the waveform determination module 430 may determine a frequency of the sine wave and a frequency of each of the one or more harmonics. As another example, the waveform determination module 430 may determine the amplitude of the sine wave and amplitude of each of the one or more harmonics. As still another example, the waveform determination module 430 may determine the reference waveform of the tube voltage based on the frequency and the amplitude of each of the one or more harmonics and the frequency and the amplitude of the sine wave.

The storage module 440 may be configured to store data and/or instructions associated with the imaging system 100. For example, the storage module 440 may store data of the reference waveform, projection data generated by one or more detectors via detecting at least a portion of the radiation rays, and/or one or more image reconstruction algorithms, etc. In some embodiments, the storage module 440 may be the same as the storage device 130 and/or the storage module 480 in the configuration.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the waveform determination module 430 may be omitted. As another example, some other components/modules may be added into the processing device 120.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 5:
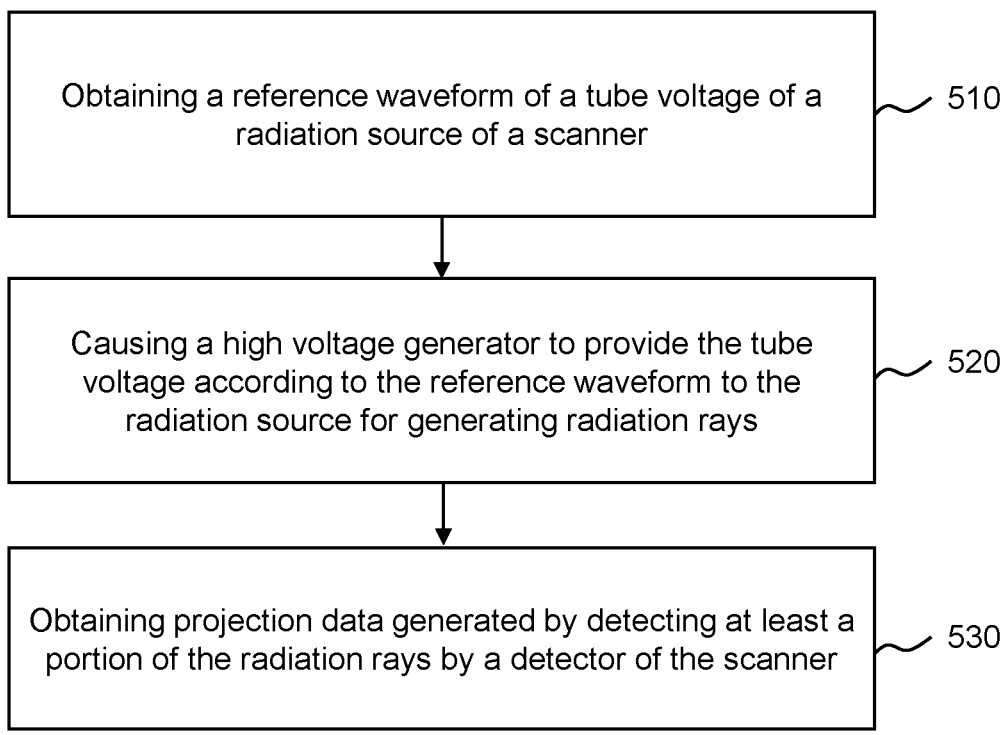
FIG. 5 is a flowchart illustrating an exemplary process for energy imaging according to some embodiments of the present disclosure.

FIG. 5 is a flowchart illustrating an exemplary process 500 for energy imaging according to some embodiments of the present disclosure. The process 500 may be executed by the imaging system 100. For example, process 500 may be implemented as a set of instructions (e.g., an application) stored in the storage device 150 in the imaging system 100. The processing device 140 may execute the set of instructions and may accordingly be directed to perform the process 500 in the imaging system 100. The operations of the illustrated process 500 presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the processing device 140 (e.g., the obtaining module 410) may obtain a reference waveform of a tube voltage of a radiation source of a scanner. The scanner may be an imaging device (e.g., the imaging device 110) including the radiation source and a detector. The radiation source may be configured to generate and/or emit radiation rays to a subject. In some embodiments, the radiation rays may include X-rays, γ-rays, α-rays, or the like, or a combination thereof. The radiation source may include a high voltage generator, a tube, etc. The high voltage generator may be configured to provide the tube voltage for the tube. The tube may be configured to generate the radiation rays based on the tube voltage. More descriptions for the imaging device and one or more components of the imaging device may be found elsewhere in the present disclosure (e.g., FIG. 1 and the descriptions thereof).

The reference waveform of the tube voltage may be used to describe a change of the tube voltage with time. The high voltage generator of the scanner may provide the tube voltage changing between a first voltage and a second voltage lower than the first voltage according to the reference waveform to the tube. The first voltage and the second voltage may be desired values of the tube voltage that the high voltage generator of the scanner may provide to the tube when an imaging scan is performed. The first voltage and/or the second voltage may be determined by an operator or according to a default setting of the imaging system 100. For example, the first voltage may be a value in a range from 120 kV to 150 kV, or in a range from 120 kV to 140 kV, etc. The second voltage may be a value in a range from 70 kV to 100 kV, in a range from 80 kV to 100 kV, etc. The reference waveform of the tube voltage may include one or more parameters, such as a frequency, an amplitude (i.e., a maximum value of the tube voltage), a minimum value of the tube voltage, etc. The reference waveform of the tube voltage may describe the tube voltage changing continuously between the maximum value and the minimum value with time. The maximum value may be the same as or close to the first voltage. The minimum value may be the same as or close to the second voltage. As used herein, a first value (e.g., the maximum value) same as or close to a second value (e.g., the first voltage) may indicate that the deviation between the first value and the second value is less than 3%, or 2%, or 1%, or 0.5%, or 0.1%, etc.

Figure 8A:
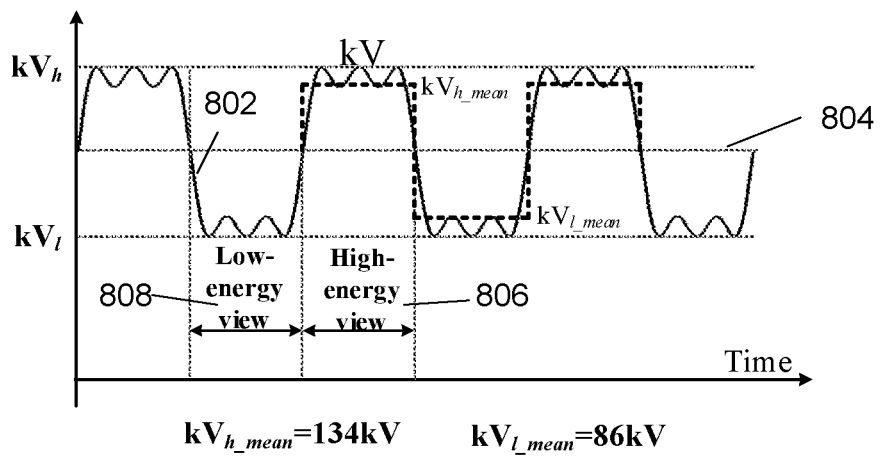
FIGS. 8A and 8B are schematic diagrams illustrating exemplary reference waveforms according to some embodiments of the present disclosure.

The reference waveform may satisfy one or more criteria. In some embodiments, the reference waveform may satisfy a first criterion that a declining speed of the tube voltage along a falling edge (e.g., the falling edge 802 of the reference waveform 800 as shown in FIG. 8A) is lower than a speed threshold. As used herein, the declining speed of the tube voltage along the falling edge may refer to a temporal change (i.e., dU/dt) of the tube voltage in a transition time decreasing from the maximum value to the minimum value.

The speed threshold may be determined by an operator or according to a default setting of the imaging system 100. For example, the speed threshold may be 400 kV/ms, or 300 kV/ms, or 200 kV/ms, or 100 kV/ms, or 40 kV/ms, etc. As another example, the speed threshold may be determined based on a first performance parameter of the controller of the high voltage generator. The first performance parameter of the controller may include a maximum declining speed of the tube voltage that the controller of the high voltage generator may realize and/or control. The maximum declining speed of the tube voltage that the controller of the high voltage generator may realize and/or control may be determined based on a ratio of a tube current of the radiation resource to an output capacitance of the high voltage generator. Further, the speed threshold may be smaller than or equal to the maximum declining speed of the tube voltage that the controller of the high voltage generator may realize and/or control.

In some embodiments, the reference waveform may satisfy a second criterion that the maximum value of the reference waveform may be equal to the first voltage. In some embodiments, the reference waveform may satisfy a third criterion that the minimum value of the reference waveform may be equal to the second voltage. In some embodiments, the reference waveform of the tube voltage may satisfy a fourth criterion. The fourth criterion may include that a spectral discrimination between a high-energy spectrum corresponding to the first voltage and a low-energy spectrum corresponding to the second voltage of radiation rays generated by the radiation source according to the reference waveform may exceed a discrimination threshold. The spectral discrimination between the high-energy spectrum and the low-energy spectrum of the radiation rays may denote a degree of difference between the high-energy spectrum and the low-energy spectrum. As used herein, the high-energy spectrum corresponding to the first voltage may describe an energy distribution of radiation rays generated when values of the tube voltage are within a range between the first voltage (or the maximum value) and a half of a sum of the first voltage (or the maximum value) and the second voltage (or the minimum value). The low-energy spectrum corresponding to the second voltage may describe an energy distribution of radiation rays generated when values of the tube voltage are within a range between the second voltage (or the minimum value) and a half of a sum of the first voltage (or the maximum value) and the second voltage (or the minimum value). In some embodiments, the spectral discrimination between the high-energy spectrum and the low-energy spectrum corresponding to the reference waveform may be denoted by a difference between a mean value of the tube voltage during a high-energy projection or view (e.g., the high-energy view 806) and a mean value of the tube voltage during a low-energy projection or view (e.g., the low-energy view 808). The greater the difference between the mean value of the tube voltage during the high-energy projection and the mean value of the tube voltage during the low-energy projection is, the greater the spectral discrimination between the high-energy spectrum and the low-energy spectrum may be. As used herein, the high-energy projection may refer to the generation of radiation rays when the tube voltage changes within the first voltage (or the maximum value) and the half of the sum of the first voltage (or the maximum value) and the second voltage (or the minimum value). The low-energy projection may refer to the generation of radiation rays when the tube voltage changes within the second voltage (or the minimum value) and the half of the sum of the first voltage (or the maximum value) and the second voltage (or the minimum value). The reference waveform may be periodic. A high-energy projection and a low-energy projection in one cycle may form an energy view. The mean value of the tube voltage corresponding to the high-energy projection (or the low-energy projection) may be equal to a ratio of the sum of values of the tube voltage in a high-energy projection (or the low-energy projection) of a cycle to a duration of a half-cycle.

The discrimination threshold may be determined by an operator or according to a default setting of the imaging system 100. For example, the discrimination threshold may be determined based on a difference between the first voltage and the second voltage. Further, the discrimination threshold may be equal to and close to the difference between the first voltage and the second voltage. In some embodiments, the discrimination threshold may be determined based on a reference spectral discrimination between a high-energy spectrum and a low-energy spectrum of radiation rays generated when the tube voltage changes between the first voltage and the second voltage according to a specific sinusoidal waveform and/or a specific rectangular waveform. For example, the discrimination threshold may be equal to or exceed the reference spectral discrimination between the high-energy spectrum and the low-energy spectrum of the radiation rays generated when the tube voltage changes between the first voltage and the second voltage according to the specific sinusoidal waveform. As another example, the discrimination threshold may be less than or close to or the reference spectral discrimination between the high-energy spectrum and the low-energy spectrum of the radiation rays generated when the tube voltage changes between the first voltage and the second voltage according to the specific rectangular waveform. A specific sine waveform and/or rectangular waveform may include a maximum value that is the same as the first voltage (or the maximum value of the reference waveform). The specific sine waveform and/or rectangular waveform may include a minimum value that is the same as the second voltage (or the minimum value of the reference waveform). The frequency of the specific sine waveform and/or the rectangular waveform may be the same as the frequency of the reference waveform. In some embodiments, the reference waveform may satisfy one of the one or more criteria (e.g., the first criterion, the second criterion, the third criterion, or the fourth criterion). In some embodiments, the reference waveform may satisfy at least two of the one or more criteria (e.g., the first criterion, the second criterion, the third criterion, and the fourth criterion).

In some embodiments, the reference waveform of the tube voltage may be formed based on a superposition of a sine wave and one or more harmonics. The sine wave may be defined by a first amplitude, a first frequency, etc. The first amplitude may be the same as or different from the maximum value of the reference waveform (or the first voltage). The first frequency may be equal to the frequency of the reference waveform. Each of the one or more harmonics may be defined by a second amplitude, a second frequency, etc. The second amplitude may be lower than the first amplitude. In other words, a ratio of the second amplitude to the first amplitude may be lower than 1. As used herein, the ratio of the second amplitude of a specific harmonic to the first amplitude of the sine wave may be also referred to as a weight of the specific harmonic with respect to the sine wave. The second frequency may be an integer multiple of the first frequency of the sine wave (i.e., the frequency of the reference waveform). The sine wave may be also referred to as a base wave. The count or number of the one or more harmonics may be a constant in a range from 1 to 3, or from 1 to 4, such as 1, or 2, or 3, or 4, etc. In some embodiments, the one or more harmonics may include one or more odd harmonics, i.e., the second frequency of each of the one or more harmonics may be an odd multiple (e.g., 3, 5, 7, etc.) of the first frequency of the sine wave. For example, the one or more harmonics may include a 3-order harmonic, a 5-order harmonic, and a 7-order harmonic whose second frequencies are 3 times, 5 times, and 7 times of the first frequency of the sine wave, respectively. In some embodiments, the one or more harmonics may include one or more even harmonics, i.e., the second frequency of each of the one or more harmonics may be an even multiple (e.g., 2, 4, 6, etc.) of the first frequency of the sine wave. For example, the one or more harmonics may include a 2-order harmonic, a 4-order harmonic, and a 6-order harmonic whose second frequencies are 2 times, 4 times, and 6 times of the first frequency of the sine wave, respectively. In some embodiments, the one or more harmonics may include one or more odd harmonics and one or more even harmonics. In some embodiments, a maximum frequency of the one or more harmonics may be smaller than a frequency threshold. The frequency threshold may be determined by an operator or according to a default setting of the imaging system 100. For example, the frequency threshold may be determined based on a second performance parameter of a controller of the high voltage generator. The second performance parameter of the controller of the high voltage generator may include a tracking ability of the controller of the high voltage generator. The tracking ability of the controller of the high voltage generator may refer to a maximum frequency that the controller of the high voltage generator may track. As a further example, the frequency threshold may be lower than or equal to the maximum frequency that the controller of the high voltage generation may track. The first frequency and the first amplitude of the sine wave and the second frequency and the second amplitude of each of the one or more harmonics may be determined such that the reference waveform satisfies at least one of the one or more criteria. More descriptions regarding the determination of the reference waveform may be found elsewhere in the present disclosure. See, e.g., FIGS. 6 and 7, and relevant descriptions thereof.

In 520, the processing device 140 (e.g., the control module 420) may cause a high voltage generator to provide the tube voltage according to the reference waveform to the radiation source for generating radiation rays.

In some embodiments, the processing device 140 may transmit the reference waveform in the form of instructions to the controller of the high voltage generator. The controller of the high voltage generator may cause the high voltage generator to generate the tube voltage according to the reference waveform in response to the receipt of an exposure instruction from the processing device 140 or the terminal 130. The high voltage generator may supply the generated tube voltage with actual values between an anode and the cathode of the tube. An electric field may be generated between the anode and the cathode of the tube as the tube voltage provided by the high voltage generator. In some embodiments, the high voltage generator may also supply a current to a cathode filament of the tube for heating the cathode filament to generate hot electrons. The hot electrons may impinge an anode target under the electric field between the anode and the cathode to generate radiation rays (e.g., X-rays).

In 530, the processing device (e.g., the obtaining module 410) may cause the scanner to perform energy imaging. In some embodiments, the scanner may include one or more detectors. The one or more detectors may absorb the energy of the at least a portion of the generated radiation rays (e.g., X rays) when the at least a portion of the radiation rays (e.g., γray) impinge on the one or more detectors. The one or more detectors may convert the absorbed energy into visible light signals. Further, the one or more detectors may convert the visible light signals into electrical signals (i.e., projection data). The projection data may indicate an attenuation (i.e., CT values) of at least a portion of the radiation rays passing through the subject. In some embodiments, in energy imaging, the projection data may include a first portion and a second portion. The first portion of the projection data may correspond to the high-energy projection as described in operation 520. The first portion of the projection data corresponding to the high-energy projection may refer to that the first portion of the projection data may be generated by the one or more detectors via receiving radiation rays corresponding to the high-energy spectrum. The second portion of the projection data may correspond to the low-energy projection as described in operation 520. The second portion of the projection data corresponding to the low-energy projection may refer to that the second portion of the projection data may be generated by the one or more detectors via receiving radiation rays corresponding to the low-energy spectrum.

The first portion and the second portion of the projection data may be used in a multi-energy spectral imaging technique, such as a dual-energy subtraction technique, etc. For example, the projection data may be used to generate and/or reconstruct one or more density images (e.g., a bone density image, a soft tissue density image, etc.) of the subject using an image reconstruction algorithm. As another example, the processing device 140 may designate multiple groups of weights to the first portion of the projection data and the second portion of the projection data. Each group of the multiple groups of weights may include a first weight to the first portion of the projection data and a second weight to the second portion of the projection data. The processing device 140 may reconstruct a series of weighted average images using an image reconstruction algorithm by weighting the first portion of the projection data and the second portion of the projection using the first weight and the second weight, respectively. The processing device 140 may reconstruct a high-energy image based on the first portion of the projection data and a low-energy image based on the second portion of the projection data using an image reconstruction algorithm. The processing device 140 may perform a dual-energy analysis operation on the series of weighted average images, the high-energy image, and/or the low-energy image. In some embodiments, the dual-energy analysis operation may include using an image optimization algorithm, a non-linear blending algorithm, etc., to obtain one or more monoenergetic images. In some embodiments, the dual-energy analysis operation may include using a differentiation algorithm to identify or differentiate certain materials or substances of the subject. In some embodiments, the dual-energy analysis operation may include using a quantification algorithm to quantify one or more substances of the subject. Exemplary image reconstruction algorithms may include using an iterative reconstruction model, a Fourier slice theorem model, a fan-beam reconstruction model, an analytic reconstruction model, an algebraic reconstruction technique (ART), a simultaneous algebra reconstruction technique (SART), a Feldkamp-Davis-Kress (FDK) reconstruction model, or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. For example, operations 520 and 530 may be integrated into one single operation. As another example, process 500 may further include reconstructing one or more images based on the projection data. However, those variations and modifications do not depart from the scope of the present disclosure.

Figure 6:
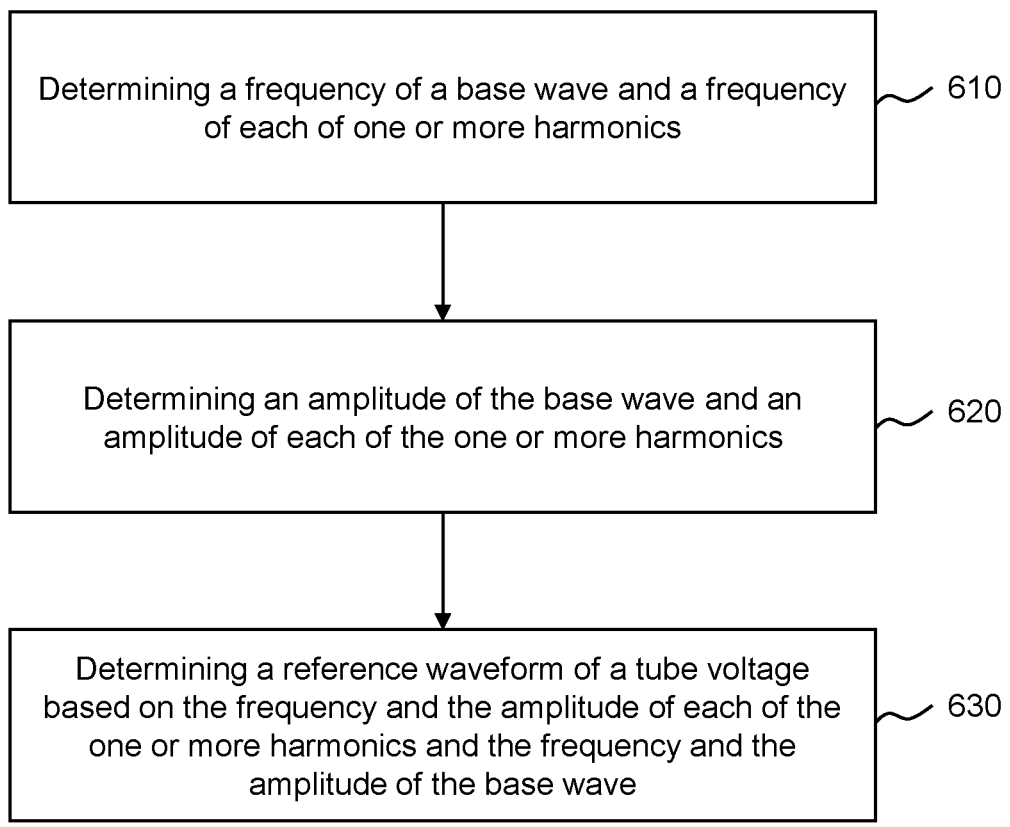
FIG. 6 is a flowchart illustrating an exemplary process for determining a reference waveform according to some embodiments of the present disclosure.

FIG. 6 is a flowchart illustrating an exemplary process 600 for determining a reference waveform according to some embodiments of the present disclosure. In some embodiments, the reference waveform may be formed based on a superposition of a sine wave and one or more harmonics. The process 600 may be executed by the imaging system 100. For example, process 600 may be implemented as a set of instructions (e.g., an application) stored in the storage device 150 in the imaging system 100. The processing device 130 may execute the set of instructions and may accordingly be directed to perform the process 600 in the imaging system 100. The operations of the illustrated process 600 presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, the processing device 140 (e.g., the waveform determination module 430) may determine a frequency of a sine wave and a frequency of each of one or more harmonics.

As used herein, the frequency of the sine wave may be also referred to as a target frequency of the sine wave. In some embodiments, the target frequency of the sine wave may be determined based on a rotation speed of a gantry of a scanner (e.g., the imaging device 110) where the radiation source is installed. The greater the rotation speed of the gantry is, the greater the target frequency of the sine wave may be. The rotation speed of the gantry may be determined by an operator or according to a default setting of the imaging system 100. In some embodiments, the target frequency of the sine wave may be determined manually by an operator (e.g., a doctor or a maintenance person), or automatically by the processing device 140, or semi-automatically by the operator and the processing device 140.

The frequency of each of the one or more harmonics may be determined at least in part based on the target frequency of the sine wave and a performance parameter of a high voltage generator. The performance parameter of the high voltage generator may include a tracking ability of a controller of the high voltage generator. The tracking ability of the controller may indicate a maximum frequency that the controller may track. The processing device 140 may determine a maximum frequency of the one or more harmonics based on the maximum frequency that the controller may track. The maximum frequency of the one or more harmonics may be an integer multiple of the target frequency of the sine wave and lower than or equal to the maximum frequency that the controller may track. The processing device 140 may determine the frequency of each of the one or more harmonics based on the maximum frequency of the one or more harmonics. For example, if the target frequency of the sine wave is f1 and the maximum frequency that the controller may track is 3.2f1, the maximum frequency of the one or more harmonics may be 3f1, and the one or more harmonics may include one single harmonic with the frequency 3f1. As another example, if the target frequency of the sine wave is f1 and the maximum frequency that the controller may track is 5.2f1, the maximum frequency of the one or more harmonics is 5f1, the one or more harmonics may include two harmonics with frequencies 3f1, and 5f1, respectively. The determined frequency of each of the one or more harmonics may be also referred to as a target frequency of each of the one or more harmonics.

In some embodiments, the processing device 140 may determine a maximum count (or number) of the one or more harmonics based on the maximum frequency of the one or more harmonics and the target frequency of the sine wave. For example, if the target frequency of the sine wave is f1 and the maximum frequency that the controller may track is 4.2f1, the maximum frequency of the one or more harmonics is 4f1, the one or more harmonics may include at most three harmonics. If the processing device 140 determines that the maximum count of the one or more harmonics is equal to 1, the processing device 140 may determine a 3-order harmonics as one single target harmonic with a target frequency 3 times of the target frequency of the sine wave. In some embodiments, if the processing device 140 determines that the maximum count of the one or more harmonics exceeds 1, the processing device 140 may determine multiple candidate groups of the one or more harmonics. Each candidate group of the multiple candidate groups of the one or more harmonics may include at least one harmonic. For example, if the one or more harmonics include odd harmonics, the target frequency of the sine wave is f1 and the maximum frequency that the controller may track is 5.2f1, the processing device 140 may determine three groups of the one or more harmonics. The three groups of the one or more harmonics may be (3-order harmonic with the frequency 3f1), (5-order harmonic with the frequency 5f1), (3-order harmonic, 5-order harmonic). In some embodiments, the processing device 140 may determine a target group from the multiple candidate groups of the one or more harmonics. The target group may include one or more target harmonics each of which with a target frequency. For example, the processing device 140 may determine one group (e.g., a group including 3-order harmonic, and 5-order harmonic among the three groups) that includes a maximum count of harmonics among the multiple candidate groups of the one or more harmonics as the target group. In some embodiments, the processing device 140 may determine a target group from the multiple candidate groups of the one or more harmonics as described in operation 620.

In some embodiments, if the processing device 140 determines that the maximum count of the one or more harmonics exceeds 1, the processing device 140 may determine the target frequency of each of the one or more harmonics based on a control difficulty coefficient corresponding to each of the one or more harmonics. For example, if the one or more harmonics includes a 3-order harmonic, a 5-order harmonic, and a 7-order harmonic according to the maximum frequency that the controller may track or the maximum frequency of the one or more harmonics. If the processing device 140 determines that a control difficulty coefficient corresponding to the 7-order harmonic exceeds a control threshold, which may be difficult to realize and/or control by the high voltage generator, the processing device 140 may remove the 7-order harmonic from the one or more harmonics and determine that the one or more harmonics may include the 3-order harmonic and the 5-order harmonic. The control difficulty coefficients of various harmonics may be a default setting of the imaging system 100.

The increase of the frequency of the harmonics may increase the control difficulty of a controller of a high voltage generator, but an improvement of a spectral discrimination spectrum of radiation rays may be gradually reduced. For example, a first reference waveform may include a superposition of a 3-order harmonic and the sine wave. A second reference waveform may include a superposition of a 3-order harmonic, a 5-order harmonic, and the sine wave. A third reference waveform may include a superposition of a 3-order harmonic, a 5-order harmonic, a 7-order harmonic, and the sine wave. The second reference waveform may correspond to a higher spectral discrimination than the first reference waveform. However, the second reference waveform may be more difficult to control and realize by the high voltage generator than the first reference waveform. The third reference waveform may be more difficult to control and realize by the high voltage generator than the second reference waveform, and spectral discriminations corresponding to the second reference waveform and the third reference waveform may be close.

In 620, the processing device (e.g., the waveform determination module 430) may determine an amplitude of the sine wave and an amplitude of each of the one or more harmonics. In 630, the processing device (e.g., the waveform determination module 430) may determine a reference waveform of a tube voltage based on the frequency and the amplitude of each of the one or more harmonics and the frequency and the amplitude of the sine wave.

In some embodiments, the amplitude of each of the one or more harmonics and the amplitude of the sine wave may satisfy a first condition that a maximum value of a reference waveform including a superposition of the sine wave and the one or more harmonics is equal to a first voltage and/or a second condition that a minimum value of the reference waveform is equal to a second voltage lower than the first voltage. The first voltage and/or the second voltage may be determined by an operator or according to a default setting of the imaging system 100 as described elsewhere in the present disclosure (e.g., FIG. 5 and the descriptions thereof). In some embodiments, the amplitude of the sine wave may be equal to the maximum value (i.e., the first voltage as described elsewhere in the present disclosure) of the tube voltage. In some embodiments, the amplitude of the sine wave and the amplitude of each of the harmonics may be determined based on the first condition. For example, the amplitude of the sine wave and the amplitude of each of the harmonics may be determined based on the maximum value (i.e., the first voltage) and/or the minimum value (i.e., the second voltage) of the reference waveform. Further, the reference waveform may be denoted by Equation (1) below:

$$Kv_{ref} = V_1 \sin \omega t + A_1 V_1 \sin(y_1 \omega t) + A_2 V_1 \sin(y_2 \omega t) \ldots + A_i V_1 \sin(y_i \omega t) \quad (1),$$

where $Kv_{ref}$ represents values of the tube voltage described by the reference waveform, $V_1$ represents the amplitude of the sine wave; $A_i V_1$ represents an amplitude of a $i^{th}$ harmonic; $A_i$ represents a weight of the amplitude of a $i^{th}$ harmonic with respect to the sine wave, and $y_i$ refers to times of the frequency of the $i^{th}$ harmonic to the target frequency of the sine wave; $\omega$ represents an angular frequency of the sine wave and the harmonics, and t refers to time.

In some embodiments, the target frequency of the sine wave and the target frequency of each of the one or more harmonics may be determined as described in operation 610. According to Equation (1), the tube voltage (or the reference waveform) may be described using a function with the amplitude of the sine wave and the weight of each of the one or more harmonics as independent variables and the value of the tube voltage as a dependent variable. The processing device 140 may determine one or more maximum points and/or one or more minimum points of the function. The processing device 140 may determine specific values of the tube voltage corresponding to the one or more maximum points and/or the one or more minimum points according to the function (or Equation (1)). The processing device 140 may consider the specific values of the tube voltage corresponding to the one or more maximum points to be equal to the maximum value (i.e., the first voltage) and/or the specific values of the tube voltage corresponding to the one or more minimum points to be equal to the minimum value (i.e., the second voltage) of the reference waveform. The processing device 140 may determine the amplitude of the sine wave and the amplitude of the one or more harmonics based on solutions of the function such that the amplitude of each of the one or more harmonics and the amplitude of the sine wave may satisfy the first condition that the maximum value of the reference waveform including the superposition of the sine wave and the one or more harmonics is equal to the first voltage and/or the second condition that the minimum value of the reference waveform is equal to the second voltage.

Figure 9:
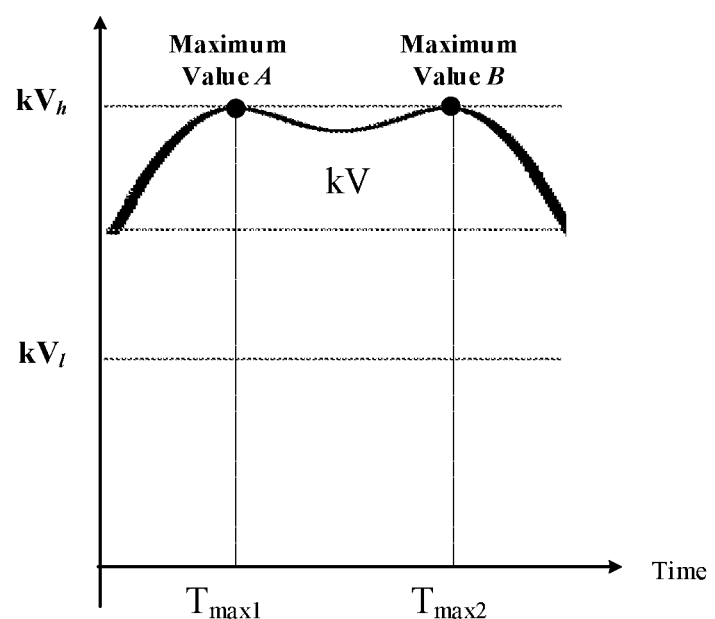
FIG. 9 is a schematic diagram illustrating a portion of an exemplary reference waveform according to some embodiments of the present disclosure.

For example, if the one or more harmonics includes a third-order harmonic, the reference waveform may be denoted by Equation (2) below:

$$Kv_{ref} = V_1 \sin \omega t + A_3 V_1 \sin(3\omega t) \quad (2),$$

where $A_3$ represents a weight of the amplitude of the 3-order harmonic with respect to the sine wave. The tube voltage (or the reference waveform) may be described using a function with the amplitude of the sine wave and the weight of 3-order harmonic as independent variables and the value of the tube voltage as a dependent variable. The processing device 140 may determine one or more maximum points $T_{max}$ (e.g., $T_{max1}$ and $T_{max2}$ as illustrated in FIG. 9) of the function. The processing device 140 may determine specific values (e.g., Maximum Value A and Maximum Value B as illustrated in FIG. 9) of the function corresponding to the one or more maximum points $T_{max}$ according to the function (or Equation (2)). The specific values of the function or the tube voltage (e.g., Maximum Value A and Maximum Value B as illustrated in FIG. 9) corresponding to the one or more maximum points $T_{max}$ (e.g., $T_{max1}$ and $T_{max2}$ as illustrated in FIG. 9) may be denoted by the weight $A_3$ of the 3-order harmonic and the amplitude $V_1$ of the sine wave. The processing device 140 may determine the weight $A_3$ of the 3-order harmonic and the amplitude of the sine wave $V_1$ by designating the specific values (e.g., Maximum Value A and Maximum Value B as illustrated in FIG. 9) of the tube voltage or function corresponding to the one or more maximum points $T_{max}$ (e.g., $T_{max1}$ and $T_{max2}$ as illustrated in FIG. 9) as the first voltage. Then, the processing device 140 may determine the reference waveform by superposing the sine wave with the determined target frequency and amplitude and the one or more harmonics each of which with the determined target frequency and amplitude.

In some embodiments, the processing device 140 may determine the multiple candidate groups of the one or more harmonics based on the maximum frequency of the one or more harmonics as described in operation 610. The processing device 140 may determine multiple candidate waveforms of the tube voltage each of which may correspond to one of the multiple candidate groups of the one or more harmonics. The processing device 140 may determine one or more target waveforms from the multiple candidate waveforms. The processing device 140 may determine the reference waveform based on the one or more target waveforms. The target waveform may correspond to a target group of the multiple candidate groups of the one or more harmonics. The target group of the multiple candidate groups of the one or more harmonics may include one or more target harmonics with target frequencies and amplitudes. For example, for each group of the multiple candidate groups of the one or more harmonics, the frequency of the each of the one or more harmonics in each group may be known. The processing device 140 may determine the amplitude of the sine wave and the amplitude of each of the one or more harmonics corresponding to each group of the multiple candidate groups of the one or more harmonics according to Equation (1) as described above. The processing device 140 may determine the multiple candidate waveforms of the tube voltage each of which may correspond to one of the multiple candidate groups of the one or more harmonics. Each of the multiple candidate waveforms of the tube voltage may be determined based on the amplitude and the target frequency of the sine wave, and the amplitude and the frequency of each of the one or more harmonics corresponding to one of the multiple candidate groups of the one or more harmonics.

In some embodiments, the processing device 140 may determine the one or more target waveforms from the multiple candidate waveforms based on a declining speed of each of the multiple candidate waveforms. The declining speed of a candidate waveform may refer to a temporal change (i.e., dU/dt) of the tube voltage along a falling edge decreasing from the maximum value to the minimum value. For example, the processing device 140 may designate one of the multiple candidate waveforms as the target waveform (i.e., the reference waveform) whose declining speed is minimum among declining speeds of the multiple candidate waveforms. The processing device 140 may designate the target waveform (i.e., the reference waveform) whose declining speed is minimum among declining speeds of the multiple candidate waveforms as the reference waveform. As another example, the processing device 140 may designate one of the multiple candidate waveforms as the one or more target waveform (i.e., the reference waveform) whose declining speed is lower than a speed threshold. The speed threshold may be determined by an operator or according to a default setting of the imaging system 100. For example, the speed threshold may be determined based on an output capacitance of the high voltage generator and a tube current of the radiation resource or the tube. As a further example, the speed threshold may be smaller than or equal to a ratio of the tube current to the output capacitance.

In some embodiments, the processing device 140 may determine at least two target waveforms from the multiple candidate waveforms whose declining speeds are lower than the speed threshold. The processing device 140 may determine one of at least two target waveforms as the reference waveform based on spectrum discriminations corresponding to the at least two target waveforms. For example, the processing device 140 may designate one of the at least two target waveforms as the reference waveform whose spectrum discrimination is maximum among the spectrum discriminations corresponding to the at least two target waveforms.

According to process 600, the reference waveform including a superposition of the sine wave and the one or more harmonics may be close to a rectangular waveform, which may improve a spectrum discrimination corresponding to the reference waveform. The maximum frequency of the one or more harmonics of the reference waveform may be determined based on a tracking ability of a controller of a high voltage generator, which may be controlled and realized easily by the high voltage generator. The reference waveform may be determined based on the output capacitance of the high voltage generator and the tube current of the radiation resource or the tube, which may be controlled and realized easily by the high voltage generator.

It should be noted that the above description is merely provided for the purposes of illustration, and not intended to limit the scope of the present disclosure. For persons having ordinary skills in the art, multiple variations and modifications may be made under the teachings of the present disclosure. For example, operations 620 and 630 may be integrated into one single operation. However, those variations and modifications do not depart from the scope of the present disclosure.

Figure 7:
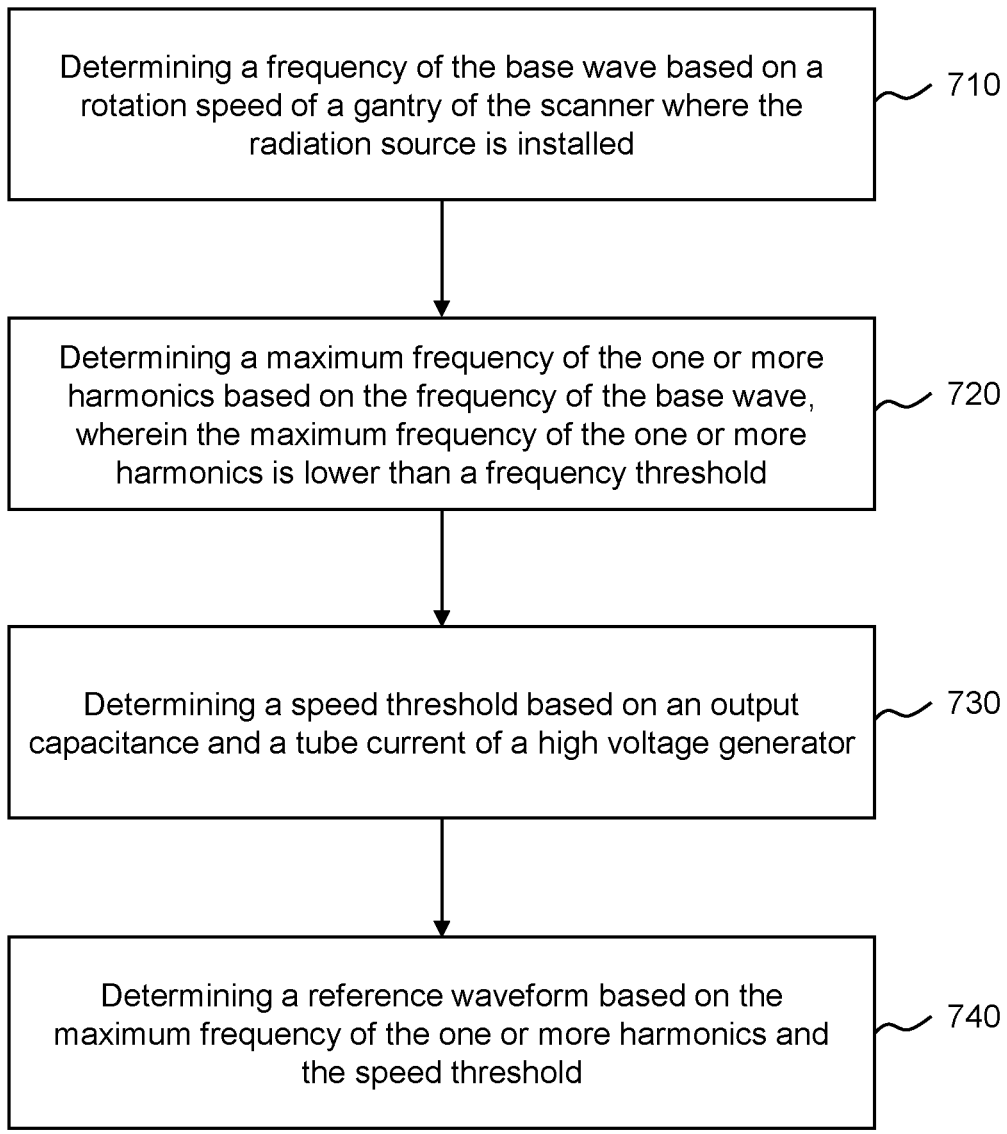
FIG. 7 is a flowchart illustrating an exemplary process for determining a reference waveform according to some embodiments of the present disclosure.

FIG. 7 is a flowchart illustrating an exemplary process 700 for determining a reference waveform according to some embodiments of the present disclosure. The process 700 may be executed by the imaging system 100. For example, process 700 may be implemented as a set of instructions (e.g., an application) stored in the storage device 150 in the imaging system 100. The processing device 140 may execute the set of instructions and may accordingly be directed to perform the process 700 in the imaging system 100. The operations of the illustrated process 700 presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the processing device 140 (e.g., the waveform determination module 430) may determine a frequency of a sine wave based on a rotation speed of a gantry of a scanner where the radiation source is installed.

In some embodiments, the frequency of the sine wave may be determined based on the rotation speed of the gantry of the scanner (e.g., the imaging device 110). The greater the rotation speed of the gantry of the scanner is, the greater the frequency of the sine wave may be. In some embodiments, the rotation speed of the gantry may be determined by an operator or according to a default setting of the imaging system 100. For example, the rotation speed may be determined based on a scanning protocol.

In 720, the processing device 140 (e.g., the waveform determination module 430) may determine a maximum frequency of the one or more harmonics based on the frequency of the sine wave. In some embodiments, the maximum frequency of the one or more harmonics may be determined based on the frequency of the sine wave and a tracking ability of a controller of a high voltage generator. The tracking ability of the controller of the high voltage generator may be denoted by a maximum frequency that the controller may track. The maximum frequency of the one or more harmonics may be an integral multiple of the frequency of the sine wave and lower than the maximum frequency that the controller may track. For example, if the frequency of the sine wave is f1 and the maximum frequency that the controller may track is 3.2f1, the maximum frequency of the one or more harmonics is 3f1. As another example, if the frequency of the sine wave is f1 and the maximum frequency that the controller may track is 4.2f1, the maximum frequency of the one or more harmonics is 4f1.

In 730, the processing device 140 (e.g., the waveform determination module 430) may determine a speed threshold based on an output capacitance and a tube current of a high voltage generator. The speed threshold may be determined based on a maximum declining speed of the tube voltage that the controller of the high voltage generator may realize and/or control. The maximum declining speed of the tube voltage that the controller of the high voltage generator may realize and/or control may be determined based on a ratio of the tube current of the radiation resource to the output capacitance of the high voltage generator. Further, the speed threshold may be smaller than or equal to the maximum declining speed of the tube voltage that the controller of the high voltage generator may realize and/or control.

In 740, the processing device 140 (e.g., the waveform determination module 430) may determine a reference waveform based on the maximum frequency of the one or more harmonics and the speed threshold.

In some embodiments, the processing device 140 may determine a maximum count (or number) of the one or more harmonics based on the maximum frequency of the one or more harmonics and the target frequency of the sine wave. For example, if the target frequency of the sine wave is f1 and the maximum frequency that the controller may track is 2.2f1, the maximum frequency of the one or more harmonics is 2f1, and the one or more harmonics may include one single harmonic with the frequency 2f1. As another example, if the target frequency of the sine wave is f1 and the maximum frequency that the controller may track is 4.2f1, the maximum frequency of the one or more harmonics is 4f1, the one or more harmonics may include at most three harmonics with the frequency 2f1, 3f1, and 4f1, respectively. In some embodiments, if the processing device 140 determines that the maximum count of the one or more harmonics exceeds 1, the processing device 140 may determine multiple candidate groups of the one or more harmonics. Each candidate group of the multiple candidate groups of the one or more harmonics may include at least one harmonic. For example, if the frequency of the sine wave is f1 and the maximum frequency that the controller may track is 5.2f1, the processing device 140 may determine three groups of the one or more harmonics. The three groups of the one or more harmonics may be (3-order harmonic with the frequency 3f1), (5-order harmonic with the frequency 5f1), and (3-order harmonic, 5-order harmonic).

The processing device 140 may determine multiple candidate waveforms of the tube voltage each of which may correspond to one of the multiple candidate groups of the one or more harmonics. For example, the processing device 140 may determine an amplitude of each of the one or more harmonics and an amplitude of the sine wave corresponding to each of the multiple candidate groups of the one or more harmonics as described in operations 620 and 630 in FIG. 6. The processing device 140 may determine each of the multiple candidate waveforms of the tube voltage based on the amplitude and the frequency of the sine wave, and the amplitude and the frequency of each of the one or more harmonics corresponding to one of the multiple candidate groups of the one or more harmonics. The processing device 140 may determine one of the multiple candidate waveforms as the reference waveform based on a declining speed of each of the candidate waveforms. The declining speed of a candidate waveform may refer to a temporal change (i.e., dU/dt) of the tube voltage along a falling edge decreasing from the maximum value to the minimum value. For example, the processing device 140 may designate one of the multiple candidate waveforms as the reference waveform whose declining speed is minimum among declining speeds of the multiple candidate waveforms. As another example, the processing device 140 may designate one of the multiple candidate waveforms as the reference waveform whose declining speed is lower than the speed threshold.

In some embodiments, the processing device 140 may determine at least two of the multiple candidate waveforms whose declining speeds are lower than the speed threshold. The processing device 140 may determine one of at least two of the multiple candidate waveforms whose declining speed is minimum as the reference waveform. The speed threshold may be determined by an operator or according to a default setting of the imaging system 100. For example, the speed threshold may be determined based on an output capacitance of the high voltage generator and a tube current of the radiation resource or the tube. As a further example, the speed threshold may be smaller than or equal to a ratio of the tube current to the output capacitance. In some embodiments, the processing device 140 may determine at least two of the multiple candidate waveforms whose declining speeds are lower than the speed threshold. The processing device 140 may determine one of at least two of the multiple candidate waveforms as the reference waveform based on spectrum discriminations corresponding to the at least two of the multiple candidate waveforms. For example, the processing device 140 may designate one of the at least two of the multiple candidate waveforms as the reference waveform whose spectrum discrimination is maximum among the spectrum discriminations corresponding to the at least two of the multiple candidate waveforms.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

EXAMPLES

The following examples are provided for illustration purposes and are not intended to limit the scope of the present disclosure.

Figure 8B:
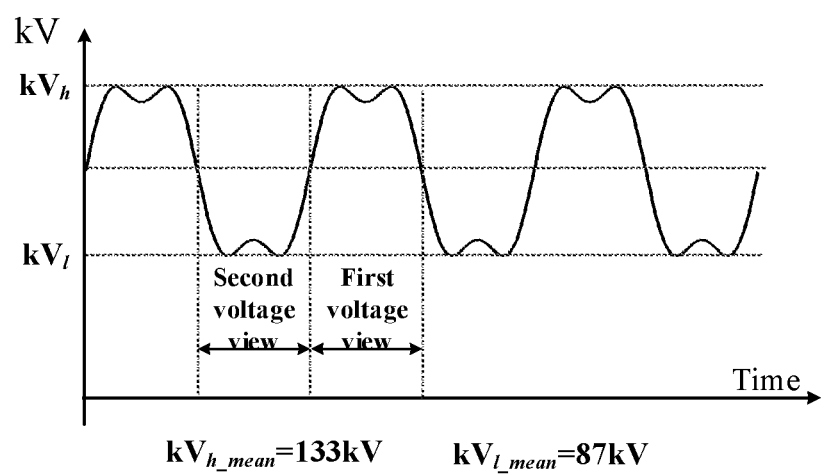

Example 1 Exemplary Reference Waveforms Formed by a Superposition of a Sine Wave and One or More Harmonics FIGS. 8A and 8B are schematic diagrams illustrating exemplary reference waveforms according to some embodiments of the present disclosure. As illustrated in FIGS. 8A and 8B, each of the reference waveform 800 and 820 is represented by a coordinate system. An X-axis of the coordinate system represents time and a Y-axis of the coordinate system represents values of a tube voltage. The reference waveform 800 is superposed by a sine wave, a 30% 3-order harmonic, and a 20% 5-order harmonic. Amplitudes of the 3-order harmonic and the 5-order harmonic are equal to 30 percent and 20 percent of the amplitude of the sine wave, respectively. Frequencies of the 3-order harmonic and the 5-order harmonic are equal to three times and five times the frequency of the sine wave, respectively.

As illustrated in FIG. 8A, the reference waveform 800 includes one or more cycles. In each cycle, the reference waveform 800 includes a high-energy view projection 806 and a low-energy view or projection 808. The high-energy view 806 in a half cycle may correspond to the tube voltage changing between a maximum value 140 kV (i.e., a first voltage) and an average value 804 of the maximum value 140 kV (i.e., a first voltage) and a minimum value 80 kV (i.e., a second voltage). The low-energy view 808 in a half cycle may correspond to the tube voltage changing between the minimum value and the average value 804 of the maximum value and the minimum value (i.e., a second voltage). A spectral discrimination between a high-energy spectrum and a low-energy spectrum of radiation rays generated according to the reference waveform 800 may be denoted by a difference between $kV_{h\_mean}$ and $kV_{l\_mean}$ in one cycle. The $kV_{h\_mean}$ denotes a mean value of the tube voltage during a duration of the high-energy view 806 and $kV_{l\_mean}$ denotes a mean value of the tube voltage during a duration of the low-energy view 808. A value of $kV_{h\_mean}$ of the reference waveform 800 is equal to 134 kV and a value of a $kV_{l\_mean}$ of the reference waveform 800 is equal to 86 kV. The spectral discrimination corresponding to the reference waveform 800 is denoted by 48 kV (i.e., 134 kV–86 kV=48 kV).

The reference waveform 820 is superposed by a sine wave and a 26.5% 3-order harmonic. An amplitude of the three-order harmonic may is equal to 26.5 percent of the amplitude of the sine wave, and a frequency of the 3-order harmonic may be equal to three times the frequency of the sine wave. The frequency and the amplitude of the sine wave of the reference waveform 820 are the same as the frequency and the amplitude of the sine wave of the reference waveform 800, respectively. As illustrated in FIG. 8B, a value of $kV_{h\_mean}$ of the reference waveform 820 is equal to 133 kV, and a value of a $kV_{l\_mean}$ of the reference waveform 820 is equal to 87 kV. A spectral discrimination between a high-energy spectrum and a low-energy spectrum of radiation rays corresponding to the reference waveform 820 is denoted by a difference between $kV_{h\_mean}$ and $kV_{l\_mean}$ in one cycle, which may be equal to 46 kV (i.e., 133 kV–87 kV=46 kV).

Comparing reference waveforms 800 and 820, the spectral discrimination corresponding to reference waveform 800 exceeds the spectral discrimination corresponding to reference waveform 820. However, the reference waveform 820 may be tracked by a controller of a high voltage generator easily as a maximum frequency (i.e., three times of the frequency of the sine wave) of the harmonics of the reference waveform 820 is lower than a maximum frequency (i.e., five times of the frequency of the sine wave) of the harmonics of the reference waveform 800.

Figure 10A:
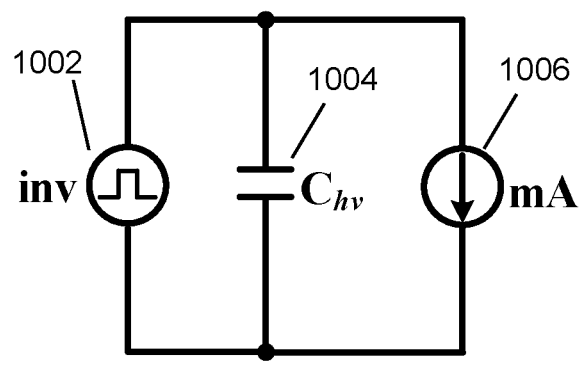
FIGS. 10A and 10B are schematic diagrams illustrating equivalent circuits associated with a high voltage generator according to some embodiments of the present disclosure.
Figure 10B:
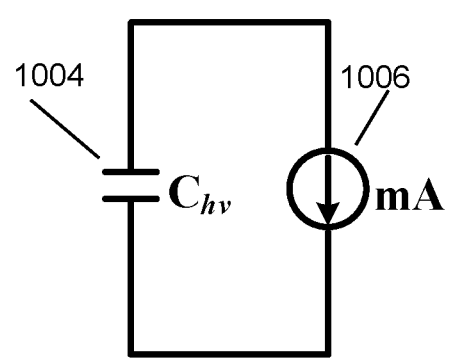

Example 2 Exemplary Equivalent Circuits Associated with a High Voltage Generator FIGS. 10A and 10B are schematic diagrams illustrating equivalent circuits associated with a high voltage generator according to some embodiments of the present disclosure. An equivalent circuit 1000 may be used for generating a tube voltage increasing from a low voltage to a high voltage. The equivalent circuit 1000 may be also referred to as a rising edge equivalent circuit 1000. As shown in FIG. 10A, the equivalent circuit 1000 may include an inverter circuit 1402 and a capacitor 1404. As a rising speed of the tube voltage may be determined based on an output capacitance of the capacitor 1404, a tube current 1006, a response speed of the inverter circuit 1402, etc., it is difficult for the high voltage generator to increase the tube voltage from the low voltage to the high voltage rapidly, which needs strict requirements for the control performance of the high voltage generator.

As shown in FIG. 10B, an equivalent circuit 1050 may be used for generating a tube voltage decreasing from a low voltage to a high voltage. The equivalent circuit 1050 may be also referred to as a falling edge equivalent circuit 1050. The declining speed of the tube voltage may be limited by an output capacitance of the capacitor 1404 and the tube current 1406.

Example 3 Exemplary Rectangular Waveform of a Tube Voltage

Figure 11A:
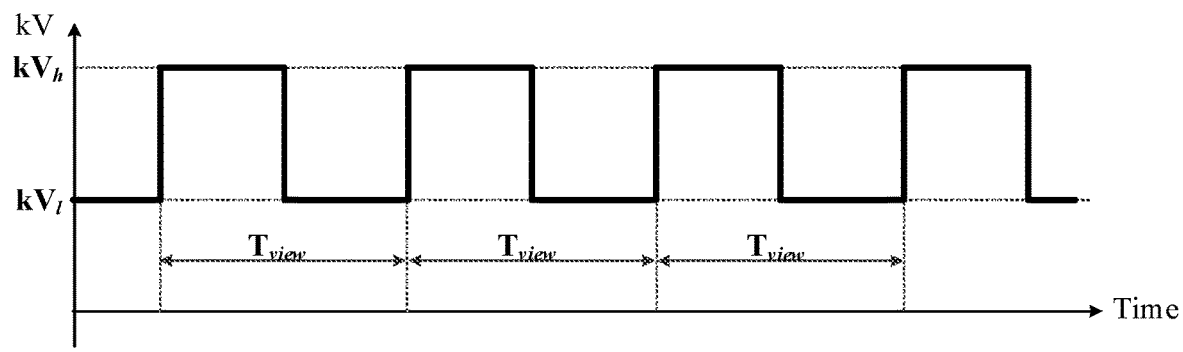
FIG. 11A is a schematic diagram illustrating an exemplary rectangular waveform according to some embodiments of the present disclosure.

FIG. 11A is a schematic diagram illustrating an exemplary rectangular waveform according to some embodiments of the present disclosure. As shown in FIG. 11A, a high voltage (i.e., maximum value) and a low voltage (i.e., minimum value) of the rectangular waveform 1100 may be the same as the maximum value 140 kV and the minimum value 80 kV of the reference waveform 800. A spectral discrimination between a high-energy spectrum and a low-energy spectrum of radiation rays generated according to the rectangular waveform 1000 is denoted by a difference between the high voltage $kV_h$ and the low voltage $kV_l$, which is equal to 60 kV. Comparing the reference waveform 800 and the rectangular waveform 1100, the spectral discrimination corresponding to rectangular waveform 1100 exceeds the spectral discrimination corresponding to reference waveform 800. However, the reference waveform 1100 is easier to be realized by a high voltage generator and the rectangular waveform 1100 is difficult to realize.

Example 4 Exemplary Trapezoidal Waveforms of a Tube Voltage

Figure 11B:
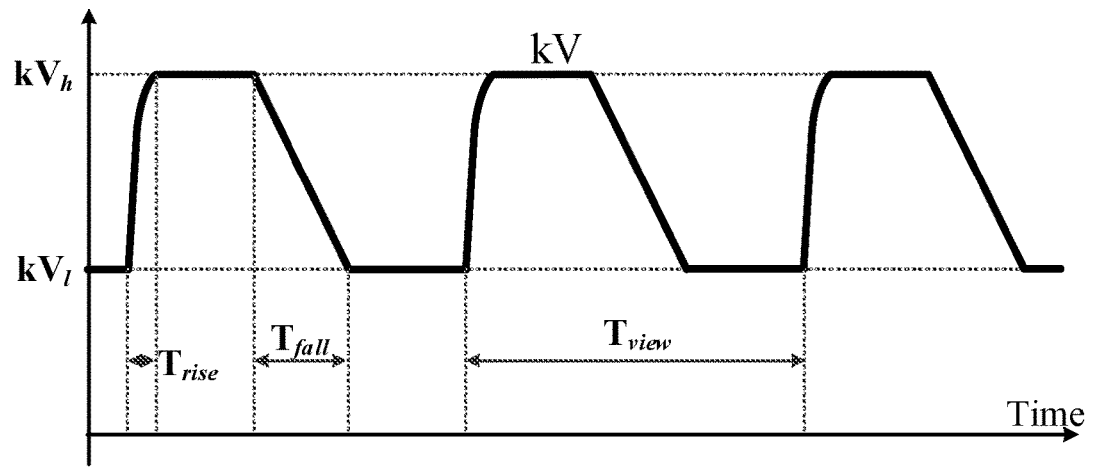
FIGS. 11B to 11D are schematic diagrams illustrating exemplary trapezoidal waveforms according to some embodiments of the present disclosure.
Figure 11C:
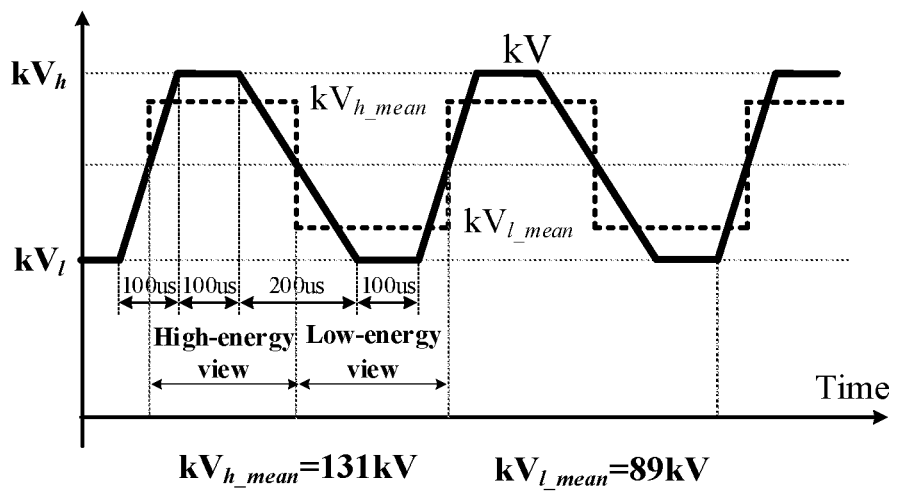
Figure 11D:
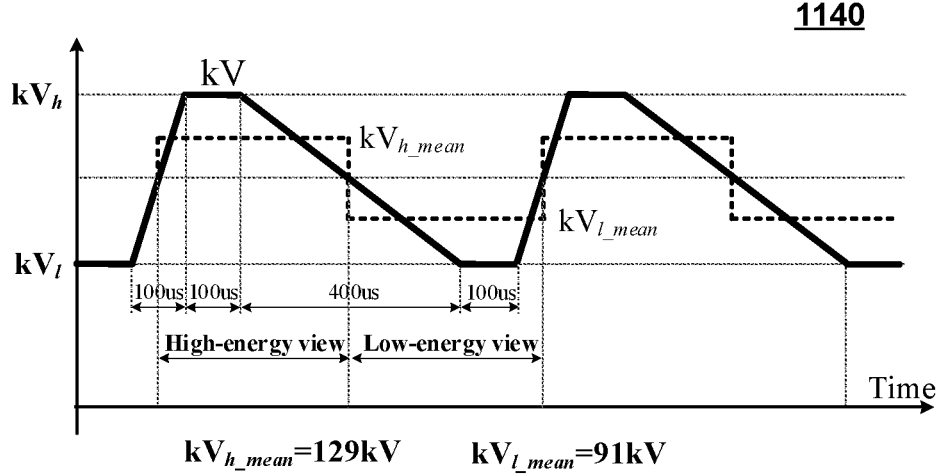

FIGS. 11B-11D are schematic diagrams illustrating exemplary trapezoidal waveforms according to some embodiments of the present disclosure. The trapezoidal waveforms 1120, 1130 and 1140 are discontinuous changing waveforms. A high voltage (i.e., maximum value) and a low voltage (i.e., minimum value) of each of the trapezoidal waveforms as shown in FIGS. 11B-11D may be the same as the maximum value of 140 kV and the minimum value of 80 kV of the reference waveform 800 and the rectangular waveform 1110.

As shown in FIG. 11C, $kV_{h\_mean}$ of the trapezoidal waveform 1130 is equal to 131 kV, and a value of a $kV_{l\_mean}$ of the trapezoidal waveform 1130 is equal to 89 kV. A spectral discrimination between a high-energy spectrum and a low-energy spectrum of radiation rays generated according to the trapezoidal waveform 1130 is denoted by a difference between $kV_{h\_mean}$ and $kV_{l\_mean}$, which is equal to 42 kV (i.e., 131 kV–89 kV=42 kV).

As shown in FIG. 11D, $kV_{h\_mean}$ of the trapezoidal waveform 1140 is equal to 129 kV, and a value of a $kV_{l\_mean}$ of the trapezoidal waveform 1140 is equal to 91 kV. A spectral discrimination between a high-energy spectrum and a low-energy spectrum of radiation rays generated according to the trapezoidal waveform 1140 is denoted by a difference between $kV_{h\_mean}$ and $kV_{l\_mean}$, which is equal to 38 kV (i.e., 129 kV–91 kV=38 kV). The spectral discriminations corresponding to the trapezoidal waveform 1130 and the trapezoidal waveform 1140 are less than the spectral discrimination corresponding to the rectangular waveform 1110 because the tube voltage needs a transition time for increasing from the minimum value to the maximum value or decreasing from the maximum value to the minimum value.

Comparing the reference waveform 800 and the trapezoidal waveforms 1130 and 1140, the spectral discrimination corresponding to the reference waveform 800 exceeds the spectral discrimination corresponding to the rectangular waveforms 1130 and 1140. And the reference waveform 800 is easier to be realized by a high voltage generator than the rectangular waveforms 1130 and 1140 as the discontinuity thereof.

Example 5 Exemplary Triangular Waveform of a Tube Voltage

Figure 11E:
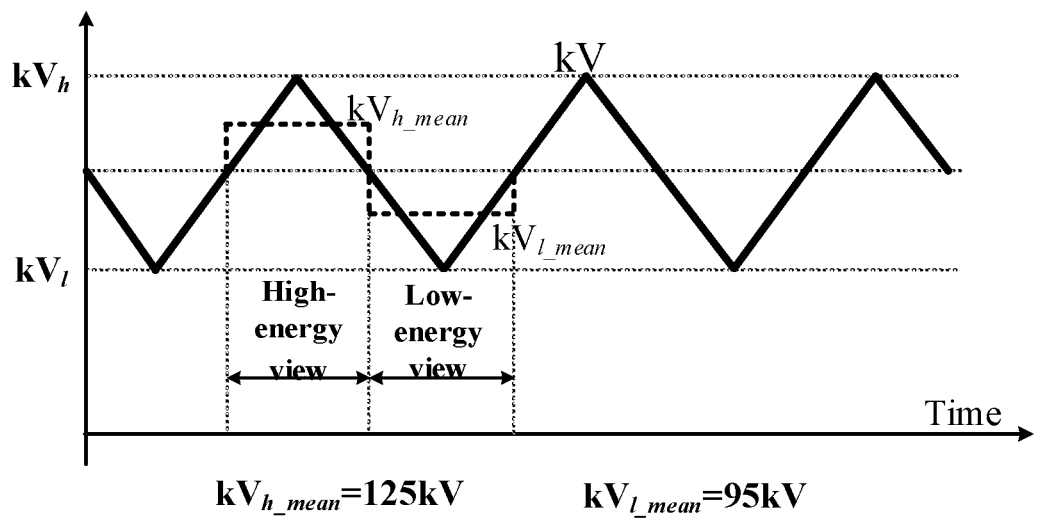
FIG. 11E is a schematic diagram illustrating an exemplary triangular waveform according to some embodiments of the present disclosure.

FIG. 11E is a schematic diagram illustrating an exemplary triangular waveform according to some embodiments of the present disclosure. In some embodiments, the triangular reference waveform may be a continuous changing waveform. A high voltage (i.e., maximum value) and a low voltage (i.e., minimum value) of the triangular waveform as shown in FIG. 11E may be the same as the maximum value of 140 kV and the minimum value of 80 kV of the reference waveform 800.

As shown in FIG. 11E, $kV_{h\_mean}$ of the triangular waveform 1150 is equal to 125 kV, and a value of a $kV_{l\_mean}$ of the triangular waveform 1150 is equal to 95 kV. A spectral discrimination between a high-energy spectrum and a low-energy spectrum of radiation rays generated according to the triangular waveform 1150 is denoted by a difference between $kV_{h\_mean}$ and $kV_{l\_mean}$, which is equal to 30 kV (i.e., 125 kV−95 kV=30 kV).

Comparing the reference waveform 800 and the triangular waveform 1150, the spectral discrimination corresponding to the reference waveform 800 exceeds the spectral discrimination corresponding to the triangular waveform 1150. And the reference waveform 800 is easier to be realized by a high voltage generator than the triangular waveform 1150 as the discontinuity thereof.

Example 6 Exemplary Sinusoidal Waveform of a Tube Voltage

Figure 11F:
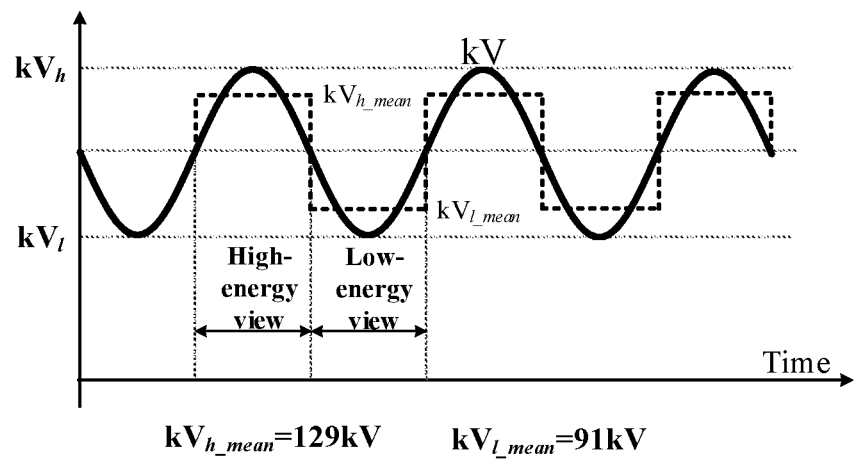
FIG. 11F is a schematic diagram illustrating an exemplary sinusoidal waveform according to some embodiments of the present disclosure.

FIG. 11F is a schematic diagram illustrating an exemplary sinusoidal waveform according to some embodiments of the present disclosure. A high voltage (i.e., maximum value) and a low voltage (i.e., minimum value) of the sinusoidal waveform 1160 as shown in FIG. 11F may be the same as the maximum value of 140 kV and the minimum value of 80 kV of the reference waveform 800.

As shown in FIG. 11F, $kV_{h\_mean}$ of the sinusoidal waveform 1160 is equal to 129 kV, and a value of a $kV_{l\_mean}$ of the sinusoidal waveform 1160 is equal to 91 kV. A spectral discrimination between a high-energy spectrum and a low-energy spectrum of radiation rays generated according to the sinusoidal waveform 1160 is denoted by a difference between $kV_{h\_mean}$ and $kV_{l\_mean}$, which is equal to 38 kV (i.e., 129 kV−91 kV=38 kV).

Comparing the reference waveform 800 and the sinusoidal waveform 1160, the spectral discrimination corresponding to the reference waveform 800 exceeds the spectral discrimination corresponding to the sinusoidal waveform 1160.

According to FIGS. 11A-11B, a rectangular waveform (e.g., the rectangular waveform 1100 as shown in FIG. 11A) of a tube voltage may be considered as an ideal waveform, which may have a high spectral discrimination between a high-energy spectrum and a low-energy energy spectrum. However, the rectangular waveform may be difficult to realize by a high voltage generator as the rise and/or the fall of the tube voltage needs time in reality. A trapezoidal waveform (e.g., the trapezoidal waveforms 1130 and 1140 as shown in FIGS. 11C and 11D) may be considered as an approximation of the rectangular waveform. The trapezoidal waveform corresponding to a high tube current (e.g., the trapezoidal waveform 1130 as shown in FIG. 11C) may have a high spectral discrimination than a trapezoidal waveform corresponding to a low tube current (e.g., the trapezoidal waveform 1140 as shown in FIG. 11D). The smaller the tube current is, the smaller the spectral discrimination of the trapezoidal waveform may be. In some embodiments, a supply of tube voltage responding to the trapezoidal waveform may be not controlled easily by a controller of a high voltage generator as the discontinuity of the trapezoidal waveform. Compared to the trapezoidal waveform and the rectangular waveform, a sinusoidal waveform (e.g., the sinusoidal waveform 1160 as shown in FIG. 11F) may be a continuously changing waveform which may be easier to be realized by the high voltage generator. The sinusoidal waveform may correspond to a fixed value of the spectral discrimination smaller than the rectangle waveform, and a supply of tube voltage corresponding to the sinusoidal waveform may be easily controlled by the controller. In some embodiments, a supply of voltage corresponding to a triangular waveform (e.g., the triangular waveform 1150 as shown in FIG. 11E) may also be easily controlled by the controller, e.g., by a hysteretic control algorithm. However, a spectral discrimination corresponding to the triangular waveform may be lower than the spectral discrimination corresponding to the sinusoidal waveform.

The switching of the tube voltage according to a discontinuously changing waveform (e.g., the trapezoidal waveform and the triangular waveform) may need to use different controllers and control parameters for different time periods, which may cause complexity, poor robustness, low stability, etc., of the high voltage generator. Additionally, the discontinuously changing waveform may be more difficult to realize as a load (e.g., a tube) and a power source (e.g., a direct power). The switching of the tube voltage according to a continuously changing waveform (e.g., the sinusoidal waveform) may be easier to control with respect to the discontinuously changing waveform, which may include an improved robustness, high stability and have a better ability to withstand disturbances from a load (e.g., a tube) and a power source (e.g., a direct power). For example, a proportional-integral-derivative controller (PID) may be used to control the switching of the tube voltage. However, the continuously changing waveform may reduce the spectral discrimination, which may affect the ability of an energy imaging technique to distinguish substances.

Accordingly, the trapezoidal waveform may provide a high spectral discrimination when a tube current is relatively high, which is difficult to be controlled by the controller of a high voltage generator, causing poor robustness and low stability. A sinusoidal waveform and a triangular waveform may be controlled easily, but spectral discriminations corresponding to the sinusoidal waveform and the triangular waveform are low. The spectral discrimination corresponding to the sinusoidal waveform may be higher than the spectral discrimination corresponding to the triangular waveform. The reference waveform determined as described elsewhere in the present disclosure (e.g., FIGS. 5 to 7 and the descriptions thereof) may be easy to control to provide a relatively high spectral discrimination.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
at least one storage device storing executable instructions, and
at least one processor in communication with the at least one storage device, when executing the executable instructions, causing the system to perform operations including:
obtaining a reference waveform of a tube voltage of a radiation source of a scanner;
causing a high voltage generator to generate the tube voltage changing according to the reference waveform; and
causing the scanner to perform energy imaging, wherein the reference waveform includes a superposition of a sine wave and one or more harmonics corresponding to the sine wave, a frequency of at least one of the one or more harmonics being an integer multiple of a frequency of the sine wave.

2. The system of claim 1, wherein obtaining a reference waveform of a tube voltage of a radiation source of a scanner, the at least one processor is further configured to cause the system to perform the operations including:
determining the frequency of the sine wave and a frequency of each of the one or more harmonics;
determining an amplitude of the sine wave and an amplitude of each of the one or more harmonics; and
determining, based on the frequency and the amplitude of each of the one or more harmonics and the frequency and the amplitude of the sine wave, the reference waveform of the tube voltage.

3. The system of claim 2, wherein to determine the frequency of the sine wave and a frequency of each of the one or more harmonics, and the at least one processor is further configured to cause the system to perform the operations including:
determining, based on a rotation speed of a gantry of the scanner where the radiation source is installed, the frequency of the sine wave;
determining, based on the frequency of the sine wave, a maximum frequency of the one or more harmonics; and
determining, at least based on in part the maximum frequency of the one or more harmonics, the frequency of each of the one or more harmonics, wherein the maximum frequency of the one or more harmonics is lower than a frequency threshold.

4. The system of claim 3, wherein the frequency threshold is defined by a tracking ability of a controller of the high voltage generator for tracking the tube voltage.

5. The system of claim 2, wherein to determine an amplitude of the sine wave and an amplitude of each of the one or more harmonics, and the at least one processor is further configured to cause the system to perform the operations including:
determining, based on the frequency of each of the one or more harmonics, the amplitude of the sine wave and the amplitude of each of the one or more harmonics, wherein the amplitude of each of the one or more harmonics and the amplitude of the sine wave are such that one or more maximum values of the reference waveform are equal to a first voltage or one or more minimum values of the reference waveform are equal to a second voltage less than the first voltage.

6. The system of claim 5, wherein a declining speed of the tube voltage when the tube voltage changes from the first voltage to the second voltage according to the reference waveform is lower than a speed threshold.

7. The system of claim 6, wherein the speed threshold is determined based on an output capacitance of the high voltage generator and a tube current of the radiation source.

8. The system of claim 1, wherein a degree of difference between energy spectrums of radiation rays generated based on the tube voltage according to the reference waveform exceeds a threshold.

9. The system of claim 8, wherein the threshold is determined based on a degree of difference between energy spectrums of radiation rays generated based on the tube voltage according to a sinusoidal waveform.

10. The system of claim 1, wherein the at least one processor is further configured to cause the system to perform the operations including:
obtaining a first portion of the projection data corresponding to a maximum value of the tube voltage changing according to the reference waveform;
obtaining a second portion of the projection data corresponding to a minimum value of the tube voltage changing according to the reference waveform; and
generating one or more images based on the first portion of the projection data and the second portion of the projection data.

11. The system of claim 1, wherein the at least one processor is further configured to cause the system to perform the operations including:
generating one or more images based on projection data generated in the energy imaging.

12. An imaging device, comprising:
a high voltage generator configured to generate a tube voltage changing according to a reference waveform;
a radiation source configured to generating radiation rays when the tube voltage is provided to the radiation source, wherein the reference waveform is formed based on a superposition of a sine wave and one or more harmonics corresponding to the sine wave, a frequency of one of the one or more harmonics being an integer multiple of a frequency of the sinewave; and
a detector configured to detect at least a portion of the radiation rays to generate projection data using an energy imaging technique.

13. A method implemented on a computing device having at least one processor and at least one storage device, the method comprising:
obtaining a reference waveform of a tube voltage of a radiation source of a scanner;
causing a high voltage generator to generate the tube voltage changing according to the reference waveform; and
causing the scanner to perform energy imaging, wherein the reference waveform is formed based on a superposition of a sine wave and one or more harmonics corresponding to the sine wave, a frequency of at least one of the one or more harmonics being an integer multiple of a frequency of the sine wave.

14. The method of claim 13, wherein obtaining a reference waveform of a tube voltage of a radiation source of a scanner includes:
determining the frequency of the sine wave and a frequency of each of the one or more harmonics;

determining an amplitude of the sine wave and an amplitude of each of the one or more harmonics; and determining, based on the frequency and the amplitude of each of the one or more harmonics and the frequency and the amplitude of the sine wave, the reference waveform of the tube voltage.

15. The method of claim 14, wherein determining the frequency of the sine wave and a frequency of each of the one or more harmonics includes:

determining, based on a rotation speed of a gantry of the scanner where the radiation source is installed, the frequency of the sine wave;

determining, based on the frequency of the sine wave, a maximum frequency of the one or more harmonics; and determining, at least based on in part the maximum frequency of the one or more harmonics, the frequency of each of the one or more harmonics, wherein the maximum frequency of the one or more harmonics is lower than a frequency threshold.

16. The method of claim 14, wherein determining an amplitude of the sine wave and an amplitude of each of the one or more harmonics includes:

determining, based on the frequency of each of the one or more harmonics, the amplitude of the sine wave and the amplitude of each of the one or more harmonics, wherein the amplitude of each of the one or more harmonics and the amplitude of the sine wave are such that one or more maximum values of the reference waveform are equal to a first voltage or one or more minimum values of the reference waveform are equal to a second voltage lower than the first voltage.

17. The method of claim 16, wherein a declining speed of the tube voltage when the tube voltage changes from the first voltage to the second voltage according to the reference waveform is lower than a speed threshold.

18. The method of claim 17, wherein the speed threshold is determined based on an output capacitance of the high voltage generator and a tube current of the radiation source.

19. The method of claim 13, wherein a degree of difference between energy spectrums of radiation rays generated based on the tube voltage changing according to the reference waveform exceeds a threshold.

20. The method of claim 19, wherein the threshold is determined based on a degree of difference between energy spectrums of radiation rays generated based on the tube voltage changing according to a sinusoidal waveform.

* * * * *